(12) United States Patent
King-Smith et al.

(10) Patent No.: US 8,470,886 B2
(45) Date of Patent: Jun. 25, 2013

(54) TOPICAL IBUPROFEN FORMULATIONS

(75) Inventors: Dominic King-Smith, San Diego, CA (US); Bradley S. Galer, West Chester, PA (US); John M. Newsam, La Jolla, CA (US); Nadir Buyuktimkin, San Diego, CA (US); Servet Buyuktimkin, San Diego, CA (US); Edward T. Kisak, San Diego, CA (US); Jagat Singh, Scarborough (CA)

(73) Assignee: NUVO Research Inc., Mississauga, Ontario (CA)

( * ) Notice: Subject to any disclaimer, the term of this patent is extended or adjusted under 35 U.S.C. 154(b) by 0 days.

(21) Appl. No.: 13/511,287

(22) PCT Filed: Nov. 26, 2010

(86) PCT No.: PCT/CA2010/001899
§ 371 (c)(1),
(2), (4) Date: May 22, 2012

(87) PCT Pub. No.: WO2011/063531
PCT Pub. Date: Jun. 3, 2011

(65) Prior Publication Data
US 2012/0232152 A1    Sep. 13, 2012

Related U.S. Application Data

(60) Provisional application No. 61/264,724, filed on Nov. 27, 2009.

(51) Int. Cl.
*A61K 31/192*    (2006.01)

(52) U.S. Cl.
USPC .......................................................... 514/570

(58) Field of Classification Search
USPC .......................................................... 514/570
See application file for complete search history.

(56) References Cited

U.S. PATENT DOCUMENTS 5,686,489 A    11/1997  Yu et al.
2010/0221245 A1    9/2010  Kunin

FOREIGN PATENT DOCUMENTS

CA    2449098    12/2002
CA    2680825    9/2008

OTHER PUBLICATIONS

International Search PCT/CA2010/001899 dated Mar. 16, 2011.

*Primary Examiner* — Raymond Henley, III
(74) *Attorney, Agent, or Firm* — Foley & Lardner LLP

(57) ABSTRACT

The present application relates to a topical formulation comprising ibuprofen, a hydroalcoholic based solvent system, a $C_{1-4}$ alcohol ester of citric acid, and a surfactant. The formulation shows physical stability over more than one month at ambient temperature and is colorless, essentially odorless, and has a pH value of about 6.5. The formulation of the application shows two to four times improved ibuprofen flux compared to a standard composition.

20 Claims, 13 Drawing Sheets

TOPICAL IBUPROFEN FORMULATIONS

The present application claims the benefit of priority from co-pending U.S. provisional patent application No. 61/264,724, filed on Nov. 27, 2009, the contents of which are incorporated herein by reference in their entirety for all purposes.

FIELD OF THE APPLICATION

The present application relates to topical ibuprofen formulations, methods for their preparation and their use for the topical treatment of pain.

BACKGROUND OF THE APPLICATION

Ibuprofen, or 2-(4-isobutylphenyl)propanoic acid, is a member of the propionic acid group of non-steroidal anti-inflammatory drugs ("NSAIDs"). Ibuprofen was originally marketed in oral form as Brufen™, and since then under various other trademarks, including Nurofen™, Advil™ and Motrin™. Ibuprofen is used for relief of symptoms of arthritis, primary dysmenorrheal, fever and as an analgesic, especially where there is an inflammatory component.

Ibuprofen occurs as [+]S- and [−]R-enantiomers and as a racemic mixture of the two. It is a white to off-white crystalline powder, practically insoluble in water (<0.1 mg/mL), but readily soluble in polar organic solvents such as ethanol and acetone.

Current topical formulations of ibuprofen that are available include, for example, Ibugel™, Ibuleve™ (5% ibuprofen gel), Deep Relief™ Dual Action Gel (5% ibuprofen, 3% levomenthol gel), Nurofen™ (10% ibuprofen gel), Booths Ibuprofen Gel (5% ibuprofen gel) and Sainsbury's Ibuprofen Pain Relief Gel (10% ibuprofen gel).

Various factors can affect the absorption rates and penetration depth of topical pharmaceutical preparations, including the nature of the active ingredient, the nature of the vehicle, the pH, and the relative solubility of the active in the vehicle versus the skin [Ostrenga J. et al., Significance of vehicle composition I: relationship between topical vehicle composition, skin penetrability, and clinical efficacy, *Journal of Pharmaceutical Sciences*, 60: 1175-1179 (1971)]. More specifically, drug attributes such as solubility, particle size and charge, as well as vehicle attributes such as the drug dissolution rate, spreadability, adhesion, and ability to alter membrane permeability can each have significant effects on penetration.

Seemingly minor variations in formulations can produce significant changes in their performance. For instance, Naito et al. demonstrates significant variability in penetration among topical NSAID formulations simply by changing the gelling agent used in the compositions [Naito et al., Percutaneous absorption of diclofenac sodium ointment, *Int. Jour. of Pharmaceutics*, 24: 115-124 (1985)]. Similarly, Ho noted significant variability in penetration by changing the proportions of alcohol, propylene glycol, and water [Ho et al., The influence of cosolvents on the in-vitro percutaneous penetration of diclofenac sodium from a gel system, [*J. Pharm. Pharmacol.*, 46:636-642 (1994)]. It was noted that the changes affected three distinct variables: (i) the solubility of the drug in the vehicle, (ii) the partition coefficient of the drug between the vehicle and the skin, and (iii) the alteration of skin structure [Id.].

Ho et al. also noted that (i) the pH of the vehicle, (ii) the drug solubility, and (iii) the viscosity of a gel matrix can influence penetration from a gel dosage form [Id.]. The pH value affects the balance between the ionized and non-ionized forms of the drug, which typically have different permeation properties [Obata, *International Journal of Pharmaceutics*, 89: 191-198 (1993)]. The viscosity can affect diffusion of the drug through the gel matrix and release of the drug from the vehicle into the skin. The solubility of the drug in the vehicle will affect the partition coefficient of the drug between the composition and the recipient membrane or tissue [Ho, Id.].

The skin barrier can be compromised by several physical methods, such as iontophoresis, ultrasound, electroporation, heat, and microneedles. Molecular penetration enhancers (MPE™s) are a preferred means for reversibly reducing the skin barrier. At least 400 chemicals have been identified as skin permeability enhancers. General categories of MPE™s include pyrrolidones, fatty acids, fatty acid esters, fatty acid alcohols, sulfoxides, essential oils, terpenes, oxazolidines, surfactants, polyols, azone and derivatives, and epidermal enzymes.

The mechanisms by which MPE™s reduce the skin barrier function are not well understood [see Williams and Barry "Penetration Enhancers" *Advanced Drug Delivery Reviews* 56: 603-618 (2004)], although it has been proposed that the mechanisms can be grouped into three broad categories: lipid disruption, increasing corneocyte permeability, and promoting partitioning of the drug into the tissue.

The challenge with use of MPE™s is that few seem to induce a significant or therapeutic enhancement of drug transport at tolerable levels. This is because an MPE™'s disruption of the skin barrier can potentially cause skin irritation, damage or both. With increased disruption, skin irritation is expected to become a greater issue. This is particularly problematic with topical pain treatments where the goal is to have the active penetrate deeply into the underlying tissue or where the drug must be used on a long-term basis due to the nature of the pain.

In light of the foregoing, there is a considerable need for the development of topical ibuprofen formulations suitable for use in the treatment of pain. The challenge has been to develop an optimal composition which will deliver the active agent to the underlying tissue in sufficient concentration to treat pain, while reducing or minimizing the incidence of skin irritation caused by disrupting the skin barrier and while providing a composition and dosage that leads to and encourages patient compliance.

SUMMARY OF THE APPLICATION

A series of hydroalcoholic-based compositions that comprise, in addition to water and alcohol(s), ibuprofen, triethyl citrate and a surfactant, have been prepared and shown to possess 2 to 4 times greater flux than a currently available standard ibuprofen topical formulations. These compositions have shown physical stability over more than one month at ambient temperature and are colourless, essentially odorless and have pH values in the range of about 3 to 7, or about 6.5.

Accordingly, the present application includes a composition comprising ibuprofen, a hydroalcoholic-based solvent, a $C_{1-4}$ alcohol ester of citric acid and a surfactant, wherein the composition is formulated for topical administration.

The presence of a $C_{1-4}$ alcohol ester of citric acid (for e.g. triethyl citrate) and a surfactant together in the composition is beneficial for ibuprofen delivery. Compositions without surfactant precipitate after about 24 hours at room temperature (RT). In the absence of triethyl citrate the compositions are not homogeneous and some reduction in permeation through the skin is observed. In the absence of both triethyl citrate and surfactant, precipitation is observed.

The present application also includes a method for treating pain comprising applying an effective amount of a topical ibuprofen composition of the application to a subject in need thereof. In one embodiment, the pharmaceutical composition is applied to the skin or mucosal surface of the subject. The skin or mucosal surface may be intact or abraded.

Also included in the present application is a use of a topical ibuprofen composition of the application to treat pain.

The present application also includes a topical ibuprofen composition of the application for use to treat pain.

The compositions of the application are useful to alleviate acute pain, chronic pain, or both. Compositions of the application are particularly suited for use in treating acute pain due to minor strains, sprains and contusions. In an embodiment of the application the pain is associated with inflammation. In a further embodiment the pain is associated with osteoarthritis.

Other features and advantages of the present application will become apparent from the following detailed description. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

The embodiments of the application will now be described in greater detail with reference to the attached drawings in which.

DETAILED DESCRIPTION OF THE APPLICATION

I. Definitions

Figure 1:
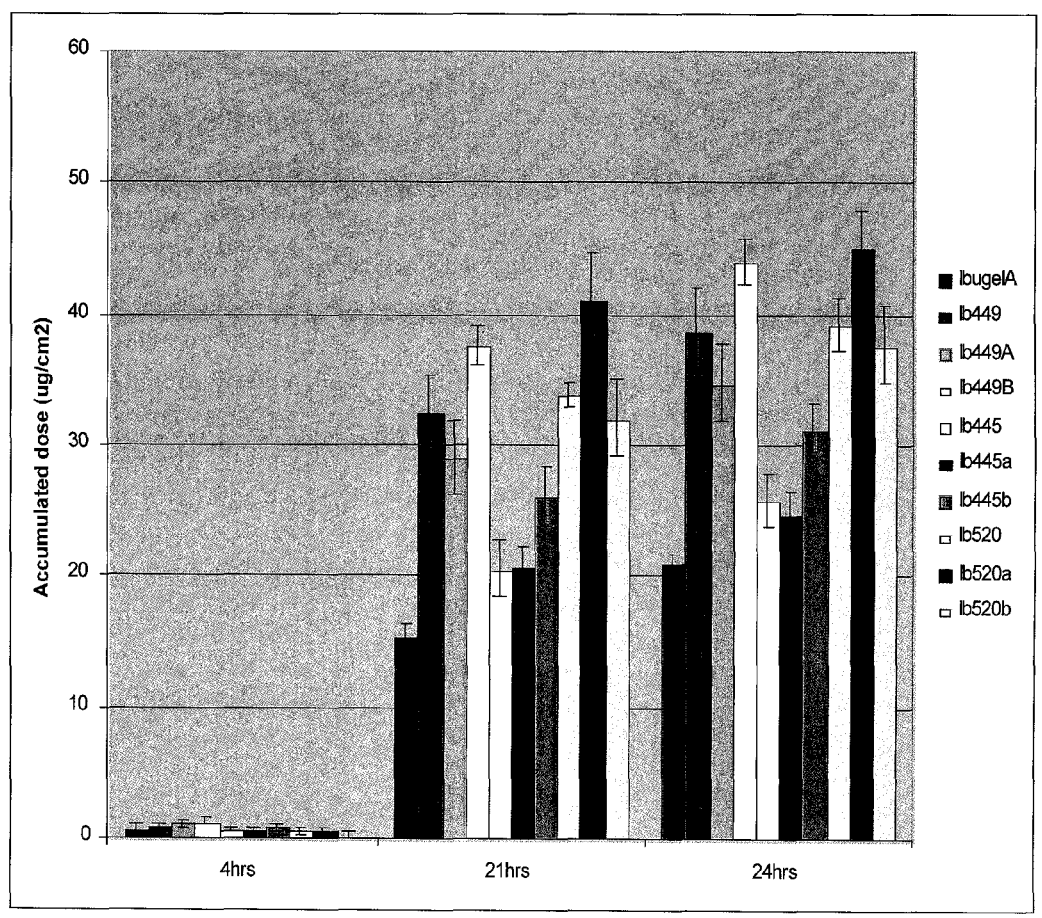
FIG. 1 is a bar graph showing the effect of thickening agents on the flux of compositions that represent embodiments of the present application. Reference is made to Table 3 for the identity and amounts of the components in the compositions.

Unless otherwise indicated, the definitions and embodiments described in this and other sections are intended to be applicable to all embodiments and aspects of the application herein described for which they are suitable as would be understood by a person skilled in the art.

The terms "a," "an," or "the" as used herein not only include aspects with one member, but also includes aspects with more than one member. For example, an embodiment including "a surfactant" should be understood to present certain embodiments with one surfactant or certain embodiment with two or more additional surfactants.

Terms of degree such as "about", "approximately" and "substantially" as used herein mean a reasonable amount of deviation of the modified term such that the end result is not significantly changed. These terms of degree should be construed as including a deviation of at least ±5% of the modified term if this deviation would not negate the meaning of the word it modifies.

In compositions comprising an "additional" or "second" component, the second component as used herein is chemically different from the other components or first component. A "third" component is different from the other, first, and second components, and further enumerated or "additional" components are similarly different.

As used herein, unless otherwise noted, the term "antisolvent" refers to a solvent which does not dissolve a specific substance and is added to a solution of said substance, directly or by vapor diffusion, to cause precipitation of said substance.

The term "agent" as used herein indicates a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "$C_{1-4}$ alcohol ester of citric acid" as used herein means a compound of the formula:

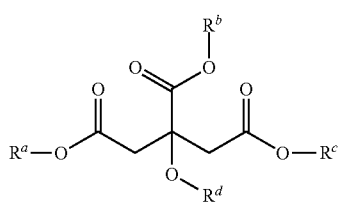

wherein at least one, two, three or four, of $R^a$, $R^b$, $R^c$ and $R^d$ are simultaneously or independently straight or branched chain $C_{1-4}$alkyl, the remainder of $R^a$, $R^b$, $R^c$ and $R^d$ being H.

"Cellulosic thickening agent" as used herein includes a thickening agent that is a natural or synthetic polymeric carbohydrate (e.g., cellulose and pharmaceutically acceptable vegetable gums) or a polymeric or oligomeric derivative of a polymeric carbohydrate that is produced by chemical modification (e.g., hydroxypropyl cellulose, hydroxypropyl methyl cellulose, hydroxyethyl cellulose). Representative cellulosic thickening agents include cellulose, hydroxypropyl cellulose ("HPC"), hydroxypropyl methyl cellulose ("HPMC"), hydroxyethyl cellulose ("HEC"), methyl cellulose, carboxymethyl cellulose, and the like.

In general, chiral compounds described herein (e.g., lactic acid), include the racemic form or the D- or the L-enantiomer thereof (e.g., D-lactic acid or L-lactic acid).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

"Enhancement ratio" ("ER") as used herein is the ratio of a test result (e.g., ug/cm$^2$ accumulated dose of product) from a formulation comprising ibuprofen to the corresponding test result from a control composition comprising ibuprofen at the same concentration in the formulation.

As used herein, the phrase "effective amount" means an amount sufficient to achieve the desired result and accordingly will depend on the ingredient and its desired result. Nonetheless, once the desired effect is known, determining the effective amount is within the skill of a person skilled in the art.

In general, the "error bars" on the graphs represent the standard error of the mean value, whereas the top of the solid, shaded bar represents a single data value, which is the mean value of the distribution of data values.

"Finite dosing" as used herein generally includes an application of a limited reservoir of an active agent. The active agent in the reservoir is depleted with time, leading to a decrease of the absorption rate of the active agent after a maximum absorption rate is reached.

"Formulation," "pharmaceutical composition," and "composition" as used herein are equivalent terms referring to a composition of matter for pharmaceutical use.

The term "hydroalcoholic" means a chassis or base solvent system that comprises a combination of water and one or more alcohols.

"Infinite dosing" as used herein generally includes an application of a large reservoir of an active agent. The active agent in the reservoir is not significantly depleted with time, thereby providing protracted, continuous, steady-state absorption of the active.

"Lower alcohol" as used herein includes straight- or branched-chain alkyl alcohols comprising 1, 2, 3, 4, 5 or 6 carbon atoms. Representative lower alcohols include methanol, ethanol, n-propanol, isopropanol, n-butanol, t-butanol, n-pentanol, 3-pentanol, 2-methoxyethanol, propylene glycol and the like.

"Monohydric alcohol" as used herein includes straight- or branched-chain alkyl alcohols with a single hydroxyl group. Representative monohydric alcohols include methanol, ethanol, n-propanol, isopropanol, n-butanol, t-butanol, n-pentanol, 3-pentanol, 2-methoxyethanol, 2-(2-ethoxyethoxy) ethanol, olelyl alcohol and the like.

"Penetration enhancer", "molecular penetration enhancer" or "MPE™" as used herein includes an agent or a combination of agents that improves the transport of molecules such as a pharmaceutically or cosmetically active agent into or through a natural membrane such as skin or nail. Various conditions may occur at different sites in the body, either in the skin or below the skin, creating a need to target delivery of compounds. For example, in a treatment for osteoarthritis, delivery of the active agent to the underlying tissues surrounding the joint may be necessary to achieve therapeutic benefit. A molecular penetration enhancer may be used to assist in the delivery of an active agent i) directly into the skin or nail; ii) locally, or regionally, into tissue(s) underlying the skin or nail; or iii) indirectly via systemic distribution to the site of the disease. If systemic distribution of an active agent (e.g., ibuprofen) would be likely to produce side effects, a molecular penetration enhancer is preferably selected to maximize direct delivery and to minimize systemic distribution. A molecular penetration enhancer may be a pure substance or may comprise, consist essentially of, or consist of a mixture of different chemical entities.

Generally, when a percentage range is defined, it incorporates all full or partial percentages in between (i.e., within the bounds of the range). For example, a percentage range of 15 to 25% would also include inter alia the specific values of 17.36% and 21%. A percentage range of about 13% to 17% would also include inter alia the specific values of 12.97%, 16%, and 17.1%.

The term "pH adjusting agent" as used herein refers to a compound added to the compositions of the present application for the purpose of changing the pH of the solution. Examples of such agents include pharmaceutically acceptable acids, pharmaceutically acceptable bases, and/or pharmaceutically acceptable buffers.

The term "pharmaceutically acceptable" means compatible with the treatment of animals, in particular, humans.

The term "pharmaceutically acceptable salt" means a pharmaceutically acceptable acid addition salt or a pharmaceutically acceptable basic addition salt. The formation of a desired compound salt is achieved using standard techniques. For example, the neutral compound is treated with an acid or base in a suitable solvent and the formed salt is isolated by filtration, extraction or any other suitable method.

The term "pharmaceutically acceptable acid addition salt" as used herein means a pharmaceutically acceptable salt of a basic compound. Basic compounds that form an acid addition salt include, for example, compounds comprising an amine group. Illustrative inorganic acids which form suitable salts include hydrochloric, hydrobromic, sulfuric and phosphoric acids. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono (such as monohydrogen orthophosphate or hydrogen sulfate) or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of an appropriate salt will be known to one skilled in the art.

The term "pharmaceutically acceptable basic addition salt" as used herein means a pharmaceutically acceptable organic or inorganic base addition salt of an acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias (such as tetraalkylammonias) or ammonia. The selection of an appropriate salt will be known to a person skilled in the art.

"Ratio", as it pertains to comparative flux values described herein, are calculated based on the cumulative amount of active (e.g. ibuprofen) delivered through the skin over a period of 4-60 hrs, preferably 24 hrs.

The term "solvate" as used herein means a compound or its pharmaceutically acceptable salt, wherein molecules of a suitable solvent are incorporated in the crystal lattice. A suitable solvent is pharmaceutically acceptable at the dosage administered. Examples of suitable solvents are ethanol, water and the like. When water is the solvent, the compound is referred to as a "hydrate". The formation of solvates will vary depending on the compound and the solvate. In general, solvates are formed by dissolving the compound in the suitable solvent and isolating the solvate by cooling or using an antisolvent. The solvate is typically dried or azeotroped under ambient conditions.

Where compounds possess more than one or more asymmetric centre, they may exist as "stereoisomers", such as enantiomers and diastereomers. It is to be understood that all such stereisomers and mixtures thereof in any proportion are encompassed within the scope of the present application. It is to be understood that while the stereochemistry of compounds may be as provided for in any given compound shown herein, such compounds may also contain certain amounts (e.g. less than 20%, less than 15%, less than 10%, less than 5% or less than 1%) of compounds having alternate stereochemistry.

The term "subject" as used herein includes all members of the animal kingdom, including mammals, and suitably refers to humans.

"Thickening agent" as used herein includes an agent or combination of agents that increases the viscosity of a composition. A thickening agent may be a pure substance, or it may comprise, consist essentially of, or consist of a mixture of different chemical entities. Exemplary thickening agents include cellulose polymers, carbomer polymers, carbomer derivatives, cellulose derivatives, polyvinyl alcohol, poloxamers, polysaccharides, and the like, as well as mixtures thereof.

"Topical formulation" as used herein includes a composition that is suitable for topical application to the skin, nail, or mucosa. A topical formulation may, for example, be used to confer a therapeutic or cosmetic benefit to its user. Specific topical formulations can be used for local, regional, or transdermal application of substances.

"Transdermal" as used herein includes a process that occurs through the skin. The terms "transdermal," "percutaneous" and "transcutaneous" can be used interchangeably. In certain embodiments, "transdermal" also includes epicutaneous.

"Transdermal application" as used herein includes administration through the skin. Transdermal application can be used for systemic delivery of an active agent; however, it is also useful for delivery of an active agent to tissues underlying the skin with minimal systemic absorption. In certain embodiments, "transdermal application" can also include epicutaneous application.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, prevention of disease spread, delaying or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. Treatment methods comprise administering to a subject a therapeutically effective amount of an active agent and optionally consists of a single administration, or alternatively comprises a series of applications. The length of the treatment period depends on a variety of factors, such as the severity of the condition, the age of the patient, the concentration, the activity of the compositions described herein, and/or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

"Triethyl citrate" as used herein means the compound of the formula:

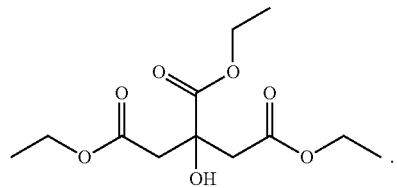

In general, the unit prefix "u" as used herein is equivalent to "μ" or "micro." For example, "ul" is equivalent to "μl" or "microliters."

The term "water" as used herein as an ingredient in the compositions of the application refers to pharmaceutically acceptable water.

The term "w/w" or "wt/wt" means a percentage expressed in terms of weight of the ingredient or agent over the total weight of the composition multiplied by 100.

II. Compositions

The present application includes a composition comprising ibuprofen, a hydroalcoholic-based solvent, $C_{1-4}$alcohol ester of citric acid and a surfactant, wherein the composition is formulated for topical administration. In an embodiment that composition is a pharmaceutical composition for human or veterinary use.

(a) Ibuprofen

The present application includes compositions comprising ibuprofen. In an embodiment, the compositions comprise a therapeutically effective amount of ibuprofen. In a further embodiment the compositions comprise a therapeutically effective amount of ibuprofen to treat pain. In another embodiment, the compositions of the present application comprise about 0.1% (w/w) to about 10% (w/w), about 0.5% (w/w) to about 9.0% (w/w), about 1.0% (w/w) to about 8.0% (w/w), about 2.0% (w/w) to about 7.0% (w/w), about 3.0% (w/w) to about 6.5% (w/w), about 4.0% (w/w) to about 6.0% (w/w) or about 5% (w/w) of ibuprofen.

In one embodiment, a composition of the present application permits delivery of an ibuprofen daily dosage of about 0.01 mg to about 1200 mg, about 0.1 mg to about 400 mg, about 1 mg to about 370 mg, about 5 mg to about 350 mg, about 10 mg to about 325 mg, about 50 mg to about 300 mg, or about 100 mg to about 250 mg, in single or divides doses. In another embodiment, the concentration of ibuprofen is such that the dosage amount can be provided by application of the composition from one to four times a day, one to three times a day, or one to two times a day, to a skin area of up to about 2500 cm², suitably about 1200 to 1800 cm². Alternatively, the composition can be applied to a skin area of about 1 to 50 cm², about 50 to 250 cm², about 100 to 500 cm², about 200 to 800 cm², or about 800 to 1200 cm². A person skilled in the art will appreciate that the dosage and application area will vary on, and can be tailored to, the area being treated.

In an embodiment of the application, the ibuprofen is racemic (R/S) ibuprofen. In a further embodiment, the ibuprofen is (S+)-ibuprofen. When the ibuprofen is used as an enantiomerically enriched substance, it is an embodiment that it also contain less than about 20%, less than about 15%, less than about 10%, less than about 5% or less than about 1% of the alternate enantiomer.

(b) $C_{1-4}$Alcohol Ester of Citric Acid

The present application includes compositions comprising a $C_{1-4}$alcohol ester of citric acid. In an embodiment of the application the $C_{1-4}$alcohol ester of citric acid is a compound of the formula:

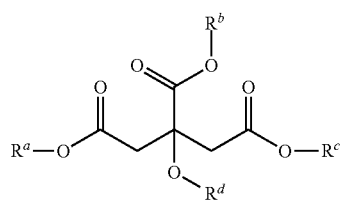

wherein at least one, two, three or four, of $R^a$, $R^b$, $R^c$ and $R^d$ are simultaneously or independently straight or branched chain $C_{1-4}$alkyl, the remainder of $R^a$, $R^b$, $R^c$ and $R^d$ being H. In a further embodiment $R^a$, $R^b$ and $R^c$ are the same and are selected from methyl, ethyl, propyl, butyl, isopropyl, isobutyl and t-butyl and $R^d$ is selected from H and methyl. In a further embodiment $R^a$, $R^b$ and $R^c$ are ethyl and $R^d$ is H (i.e. triethyl citrate).

Without being bound by theory, the $C_{1-4}$alcohol ester of citric acid of the application may function to aid in the homogeneity of the composition. The $C_{1-4}$alcohol ester of citric acid of the application may additionally or alternatively function as a molecular penetration enhancer (MPE™).

In an embodiment, the compositions comprise an effective amount of a $C_{1-4}$alcohol ester of citric acid. In the absence of a $C_{1-4}$alcohol ester of citric acid, such as triethyl citrate, the compositions are not homogeneous and a slight reduction of permeation is observed. In an embodiment, the compositions comprise an amount of a $C_{1-4}$alcohol ester of citric acid (e.g triethyl citrate) that is effective to improve the homogeneity and stability of the composition compared to an otherwise identical comparative composition that lacks a $C_{1-4}$alcohol ester of citric acid (e.g. triethyl citrate). In another embodiment, the compositions of the present application comprise about 0.5% (w/w) to about 5% (w/w), about 1.5% (w/w) to about 4.5% (w/w), about 2.0% (w/w) to about 4.0% (w/w) or about 3% (w/w) of the $C_{1-4}$alcohol ester of citric acid, for e.g. triethyl citrate.

(c) Surfactants

The present application includes compositions comprising at least one surfactant or surface active agent. In certain aspects, the surfactant may additionally or alternately function as a molecular penetration enhancer (MPE™).

In an embodiment the surfactant is an ionic surfactant such as an anionic surfactant or a zwitterionic (or amphoteric) surfactant or a mixture thereof. Examples of anionic surfactants include, for example, those comprising a sulfate anion such as sodium lauryl sulfate, ammonium lauryl sulfate, sodium dodecyl sulfate and other alkyl sulfate salts, or mixtures thereof. Examples of zwitterionic surfactants include, for example, the N-(cocoalkyl)amidopropyl betaines having the general formula:

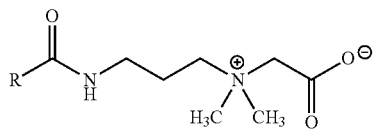

wherein R is an alkyl chain comprising 9, 11, or 13, suitably 11 carbon atoms. In one embodiment, the zwitterionic surfactant is the cocoamidopropyl betaine, {[3-(dodecanoylamino)propyl](dimethyl)ammonio}acetate (Amphosol®).

In an embodiment the surfactant is present in the compositions of the application in an effective amount. In a further embodiment, the effective amount is an amount that causes a decrease in precipitation in the composition compared to an otherwise identical comparative composition that lacks the surfactant.

In an embodiment, the compositions of the present application comprise about 0.5% (w/w) to about 20% (w/w), about 0.75% (w/w) to about 15% (w/w), about 1.0% (w/w) to about 10% (w/w), about 1.5% (w/w) to about 9% (w/w) or about 2.0% (w/w) to about 8.0% (w/w) of one or more surfactants.

In an embodiment of the application, the compositions comprise an anionic surfactant, for example sodium lauryl sulfate, as the only surfactant. When the compositions comprise sodium lauryl sulfate as the only surfactant, it is an embodiment that the composition comprises about 0.5% (w/w) to about 5% (w/w), about 1.0% (w/w) to about 4.0% (w/w), about 1.5% (w/w) to about 3.0% (w/w) or about 2% (w/w) of this surfactant.

In another embodiment of the application, the compositions comprise a zwitterionic surfactant, for example N-(cocoalkyl)amidopropyl betaines, as the only surfactant. When the compositions comprise N-(cocoalkyl) amidopropyl betaines as the only surfactant, it is embodiment that the composition comprises about 1.0% (w/w) to about 10% (w/w), about 2.0% (w/w) to about 9.0% (w/w), about 3.0% (w/w) to about 8.0% (w/w) or about 4.0% (w/w) to about 6.0% (w/w) of this surfactant.

In another embodiment, the compositions of the present application comprise both an anionic and a zwitterionic surfactant, for example sodium lauryl sulfate and an N-(cocoalkyl)amidopropyl betaine. When the compositions comprise both an anionic and a zwitterionic surfactant, it is an embodiment that the composition comprises about 2.0% (w/w) to about 10% (w/w), about 3.0% (w/w) to about 9.0% (w/w) or about 4.0% (w/w) to about 8.0% (w/w) of combined total surfactant. It is a further embodiment that the ratio of zwitterionic to anionic surfactant be about 10:1 to about 2:1 or about 4:1.

In certain embodiments the compositions of the present application further comprise a nonionic surfactant. Examples of nonionic surfactants include, but are not limited to alkyl poly(ethylene oxide), poloxamers, alkyl polyglcosides, fatty alcohols, polysorbates, glycerine esters such as glycerin ricinoleate and glycerin monolaurate, and alkyl-poly(ethylene oxide) ethers (e.g. Brij™ surfactants), and mixtures thereof. Nonionic surfactants can also act as emulsifiers. In an embodiment, the nonionic surfactant is present in the composition in an amount of about 0.1% (w/w) to about 20% (w/w), about 1.0% (w/w) to about 15% (w/w) or about 2.0% (w/w) to about 10.0% (w/w).

When the compositions further comprise a nonionic surfactant, it is embodiment that the composition comprises about 0.5% (w/w) to about 20% (w/w), about 0.75% (w/w) to about 15% (w/w), about 1.0% (w/w) to about 10% (w/w), about 2.0% (w/w) to about 9.0% (w/w), about 3.0% (w/w) to about 8.0% (w/w) or about 4.0% (w/w) to about 6.0% (w/w) of combined total surfactant.

(d) Solvents

The compositions of the present application are based on a hydroalcoholic chassis, and therefore comprise, as the main solvent, a mixture of water and an alcohol. It is an embodiment of the present application that the compositions comprise about 10% (w/w) to about 60% (w/w), about 15% (w/w) to about 55% (w/w) or about 20% (w/w) to about 50% (w/w) of water and about 10% (w/w) to about 60% (w/w), about 15% (w/w) to about 55% (w/w) or about 20% (w/w) to about 50% (w/w) of alcohol.

In an embodiment, the water component of the hydroalcoholic chassis is buffered. Alternately or additionally, the water component is adjusted with a pH adjusting agent.

In an embodiment, the alcohol is a lower alkyl alcohol or a mixture of lower alkyl alcohols. In a further embodiment, the alcohol is a monohydric alcohol. In a further embodiment, the alcohol is ethanol, isopropanol, or 2-(2-ethoxyethoxy)ethanol (transcutol), or a mixture thereof.

In another embodiment, the lower alcohol is a diol, or a mixture thereof. Alternatively, the composition additionally comprises a diol. Suitable diols include, but are not limited to, propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol, and mixtures thereof. In an embodiment, the diol is propylene glycol. In one embodiment, the formulation comprises about 0% (w/w) to about 20% (w/w), about 1.0% (w/w) to about 15% (w/w) or about 4% (w/w) to about 15% (w/w) of propylene glycol.

In a further embodiment of the application, the composition further comprises additional solvents. Examples of suitable additional solvents include, but are not limited to, D-panthenol, dimethylsulfoxide (DMSO) and dimethylacetamide (DMA), and mixtures thereof. When additional solvents are included in the compositions of the present application, it is an embodiment that they are present in an amount of about 0% (w/w) to about 20% (w/w), about 1.0% (w/w) to about 15% (w/w) or about 4% (w/w) to about 15% (w/w).

Without being bound by theory, it is a further aspect of the application that the solvent can additionally or alternately function as a molecular penetration enhancer (MPE™).

(e) Other Ingredients

The compositions of the present application further include at least one other pharmaceutically acceptable agent or excipient.

In an embodiment, the compositions of the present application include a pH adjusting agent. In a further embodiment, the pH adjusting agent is present in an effective amount. In an embodiment, the pH adjusting agent adjusts the pH so that ibuprofen is in a protonated form. Accordingly the pH adjusting agent is present in an amount effective to keep ibuprofen in a protonated form.

In one particular embodiment, the pH-adjusting agent is a base. Suitable pH-adjusting bases include bicarbonates, carbonates, hydroxides (such as ammonium hydroxide, alkali or alkaline earth metal hydroxides as well as transition metal hydroxides), and the like. In an alternative aspect, suitable pH-adjusting bases include amines, such as diethanolamine, triethanolamine, or aminopropanol. Additionally or alternatively, the pH-adjusting agent can be an acid, an acid salt, or mixtures thereof. In an embodiment, the pH-adjusting agent comprises two agents (e.g., sodium hydroxide and hydrochloric acid) that are included as needed to adjust the final pH of the composition to a desired pH.

In an embodiment, the pH adjusting agent is lactic acid. In an further embodiment, the composition comprises about 0.1% (w/w) to about 5% (w/w), about 0.25% (w/w) to about 4% (w/w), about 0.5% (w/w) to about 3.0% (w/w), about 0.75% (w/w) to about 2.0% (w/w) or about 1.0% (w/w) of a pH adjusting agent, suitably lactic acid.

In certain aspects, the lactic acid is racemic (i.e., racemic lactic acid). Alternatively, the lactic acid is enantiomerically enriched or is substantially a single enantiomer (e.g., (S)-lactic acid, also termed L-lactic acid). In an embodiment, the lactic acid is L-lactic acid. In other embodiments, the lactic acid additionally or alternatively functions as a molecular penetration enhancer (MPE™).

Other pH adjusting agents can also be used, including other acid, acid salts, or mixtures thereof. Further, the pH adjusting agent can additionally or alternately be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers and the like. In one embodiment, the buffer is phosphate buffered saline (PBS). In an alternate embodiment, the buffer is a citrate buffer. In a further embodiment, the buffer comprises or is included in the water component of the hydroalcholic chassis.

In an embodiment, the inventive formulation includes a buffer, and a second pH-adjusting agent (e.g., sodium hydroxide or hydrochloric acid) to adjust the pH of the composition to a desired pH. More preferably, the second pH-adjusting agent comprises two agents (e.g., sodium hydroxide and hydrochloric acid) that are included as needed to adjust the pH of the hydroalcoholic chassis and/or final composition to a desired pH.

In an embodiment, the compositions of the present application comprise at least one thickening agent, for example, a cellulosic thickening agent. The addition of thickeners did not cause a direct effect on the ibuprofen flux but provided a more viscous composition that is suitable for gel topical formulations. Suitable cellulosic thickening agents include, but are not limited to, hydroxypropyl cellulose (HPC) of various grades, hydroxypropyl methyl cellulose, hydroxyethyl cellulose, hydroxyethyl methyl cellulose, ethyl cellulose, methyl cellulose, carboxymethyl cellulose, dextran, guar gum, pectin, starch, cellulose, and the like, and mixtures thereof. In an embodiment, the cellulosic thickening agent is HPC.

In a further embodiment, the composition comprises about 0.0% (w/w) to about 5% (w/w), about 0.1% (w/w) to about 4% (w/w), about 0.5% (w/w) to about 3.0% (w/w), about 0.75% (w/w) to about 2.0% (w/w) or about 1.0% (w/w) of a thickening agent, suitably a cellulose thickening agent.

In another embodiment, the compositions of the present application further comprise a humectant, emollient and/or a moisturizer. An example of such a compound is D-panthenol. The addition of D-panthenol also reduces precipitation. In an embodiment the compositions of the present application comprise 0.0% (w/w) to about 10% (w/w), about 1.0% (w/w) to about 9% (w/w), about 2.0% (w/w) to about 8.0% (w/w), about 3.0% (w/w) to about 7.0% (w/w), about 4.0% (w/w) to about 6.0% (w/w) or about 5% (w/w) of D-panthenol.

In another embodiment, the compositions of the present application additionally comprise a terpene. In a further embodiment the terpene is a monoterpene such as limonene or α-terpineol, or a mixture thereof. In certain embodiments the presence of one or more terpenes in the compositions enhance the activity of the composition. As such, the terpene may function as an MPE™. In a further embodiment, the one or more terpenes are present in the composition in an amount of about 0.0% (w/w) to about 10% (w/w), about 1.0% (w/w) to about 9% (w/w), about 2.0% (w/w) to about 8.0% (w/w), about 3.0% (w/w) to about 7.0% (w/w), about 4.0% (w/w) to about 6.0% (w/w) or about 5% (w/w).

It certain embodiments, urea is added to the compositions of the present application. In a further embodiment, urea is present in the composition in an amount of about 0.0% (w/w) to about 10% (w/w), about 1.0% (w/w) to about 9% (w/w), about 2.0% (w/w) to about 8.0% (w/w), about 3.0% (w/w) to about 7.0% (w/w), about 4.0% (w/w) to about 6.0% (w/w) or about 5% (w/w).

In a further embodiment, the compositions of the present application additionally comprises an anti-oxidant. Suitable anti-oxidants for use in the present invention include, but are not limited to, butylated hydroxytoluene, butylated hydroxyanisole, ascorbyl linoleate, ascorbyl dipalmitate, ascorbyl tocopherol maleate, calcium ascorbate, carotenoids, kojic acid and its pharmaceutically acceptable salts, thioglycolic acid and its pharmaceutically acceptable salts (e.g., ammonium salts), tocopherol, tocopherol acetate, tocophereth-5, tocophereth-12, tocophereth-18, tocophereth-80 and the like, and mixtures thereof.

In still another embodiment, the composition additionally comprises a chelating agent. Suitable chelating agents include, but are not limited to, ethylenediamine tetraacetic acid (EDTA), diammonium EDTA, dipotassium EDTA, calcium disodium EDTA, H-EDTA, TEA-EDTA, tetrasodium EDTA, tripotassium EDTA, trisodium phosphate, diammonium citrate, galactaric acid, galacturonic acid, gluconic acid, glucuronic acid, humic acid, cyclodextrin, potassium citrate, the potassium salt of ethylenediamine-tetra (methylene phosphonic acid) (EDTMP), sodium citrate, sodium EDTMP, and the like, and mixtures thereof.

In yet another embodiment, the composition additionally comprises a preservative, such as propyl paraben or methyl paraben, or combinations thereof. The formulation may be made bacteriostatic by the addition of preservatives. For example, a composition can contain about 0.001 to 8%, about 0.01 to 6%, or about 0.05 to 5% (w/w) of a preservative or a combination of preservatives. A variety of preservatives are suitable, including, but not limited to, benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, diethylene glycol dimethyl ether ("DEDM") hydantoin, DEDM hydantoin dilaurate, dehydroacetic acid, dibromopropamidine diisethionate, and 1,3-bis(hydroxymethyl)-5,5-dimethylimidazolidine-2,4-dione ("DMDM") hydantoin, and mixtures thereof.

(f) Other Properties

In still yet another embodiment of the present application, the composition is selected from a spray, a gel, a cream, an emulsion, a microemulsion, a lotion, an organogel, an ointment, a solution (e.g., a moderate to highly viscous solution), and a transdermal patch. In a further embodiment, the composition is a gel, for example, a low-viscosity gel, or a spray.

In certain other embodiments, the composition is designed for high penetration, for high retention in the skin, or for both high penetration and high retention. The optimal composition will have a balance between penetration and retention, enabling an effective amount of the active ingredient to pass through the skin, but also enabling it to stay in the target area for a sufficient duration to alleviate the patient's pain or other symptoms.

In another embodiment, the composition is designed for topical efficacy with minimal systemic distribution of the active through the body by the circulatory system (e.g., the cardiovascular system). The optimal composition will have low systemic bioavailability, but will effectively treat pain or other symptoms associated with the site of application.

In yet another embodiment, the composition of the present application has a flux (as determined by the finite dosing Franz cell procedure of Example 2) equal to or greater than the flux of a known comparative composition. Suitably, the flux is greater than the flux of a comparative composition. Suitably, the flux is at least 1.5 times greater than the comparative composition's flux. In other words the ratio of (i) the composition of the present application's ibuprofen flux to (ii) the comparative composition's flux is suitably greater than 1.0, and more suitably greater than 1.5.

In a further embodiment, the composition of the present application has an ibuprofen flux that is at least 2.0, 3.0 or 4.0 times greater than the ibuprofen flux of the comparative composition.

In an embodiment, the comparative composition is a topical aqueous/alcoholic gel comprising ibuprofen (5% wt/wt), ethanol, carbomer, propylene glycol, diethylamine and purified water. An example of such a composition is Ibugel™ available from Dermal Laboratories in the United Kingdom.

In another alternative embodiment, the present application includes a solution formulation comprising ibuprofen and having a flux as determined by the multiple finite dosing Franz cell procedure (see Example 2) of at least 0.1 µg/hr/cm$^2$ at 24 hours or at least 0.2 µg/hr/cm$^2$ at 24 hours.

In still another embodiment, the composition comprising ibuprofen has an enhancement ratio (ER) of at least 1.5. In yet another embodiment, the composition comprising ibuprofen has an ER of at least 2.0. In still another embodiment, the composition comprising ibuprofen has an ER that is at least 2.5.

In still another embodiment, the formulation comprising ibuprofen provides additional advantages in comparison to previously described ibuprofen compositions. Such advantages may include one or more of the following: adhering well to the skin, spreading easily, drying more quickly, and showing greater in vivo absorption. In some more specific embodiments, the drying rate of the formulation is less than 20 minutes.

In yet another embodiment, the composition of the present application is more viscous than water at standard temperature and pressure (STP). Alternatively, the composition has a kinematic viscosity of more than about 1 centistokes (cSt) or a dynamic viscosity of more than about 1 centipoise (cP). In certain embodiments, the dynamic viscosity of the composition is at most about 2, 3, 4, 5, 7, 10, 12, 15, 20, 25, 30, 35, 40, 45, 50, 60, 70, 75, 80, 90, 100, 150, 200, 250, 500, 1000, 2000, 3000, 5000 or 10,000 cP at STP. In further embodiments, the dynamic viscosity is at most about 2, 3, 4, 5, 7, 10, 12, 15, 20, 25, 30, 35, 40, 45 or 50 cP at STP. In still further embodiments, the dynamic viscosity is at most about 2, 3, 4, 5, 7, 10, 12, 15 or 20 cP at STP. In yet other embodiments, the composition is thixotropic (i.e., it decreases in viscosity upon being stirred or shaken). The composition's viscosity can be adjusted by the addition of a thickening agent, such as a cellulosic thickening agent, for example, hydroxypropyl cellulose, or other thickening agents, or mixtures thereof.

In another embodiment, the composition is acidic. In certain embodiments, the composition has a pH of below about 7.5, of below about 6.5, of below about 5.5, of below about 4.5, of below about 3.5, or of below about 2.5. In certain other embodiments, the pH of the composition ranges from about 1.5 to about 7, about 2 to about 7, about 3 to about 7, about 4 to about 7, or about 5 to about 7, or is about 6.5.

In further embodiments, the composition remains stable for an acceptable time period between preparation and use when stored in a closed container at normal ambient temperature. In an embodiment, an "acceptable time period" is at least about 30 days, at least about six months, at least about one year, or at least about two years.

In an alternative embodiment, the application provides a formulation that degrades by less than 1% over the course of 6 months at room temperature. In an embodiment, the rate of degradation is less than about 0.9, 0.8, 0.7, 0.6, 0.5, 0.4, 0.3, 0.2, or less than 0.1%, and all fractions in between, over the course of six months at room temperature.

(g) Specific Formulations

In an embodiment of the present application, there is included a pharmaceutical composition comprising, consisting essentially of or consisting of ibuprofen, ethanol, water, triethyl citrate, lactic acid and sodium lauryl sulfate. Accordingly, the present application includes a pharmaceutical composition comprising, consisting essentially of or consisting of:

(a) about 1% (w/w) to about 10% (w/w) ibuprofen;
(b) about 40% (w/w) to about 50% (w/w) ethanol;
(c) about 40% (w/w) to about 50% (w/w) water;
(d) about 2% (w/w) to about 5% (w/w) triethyl citrate;
(e) about 0.5% (w/w) to about 2.5% (w/w) lactic acid; and
(f) about 1% (w/w) to about 3% (w/w) sodium lauryl sulfate.

In another embodiment of the above composition, the ethanol is replaced with a mixture of alcohols. In a further embodiment the mixture of alcohols comprises alcohols selected from ethanol, a polyglycol and transcutol. Accordingly, the present application also includes a pharmaceutical composition comprising, consisting essentially of or consisting of:

(a) about 1% (w/w) to about 10% (w/w) ibuprofen;
(b) about 15% (w/w) to about 25% (w/w) ethanol;
(c) about 10% (w/w) to about 20% (w/w) transcutol;
(d) about 5% (w/w) to about 15% (w/w) propylene glycol;
(e) about 25% (w/w) to about 45% (w/w) water;
(f) about 1% (w/w) to about 5% (w/w) triethyl citrate;
(g) about 0.5% (w/w) to about 2.5% (w/w) lactic acid; and
(h) about 1% (w/w) to about 3% (w/w) sodium lauryl sulfate.

In another embodiment of the present application, there is included a pharmaceutical composition comprising, consisting essentially of or consisting of ibuprofen, ethanol, water, triethyl citrate, lactic acid, propylene glycol, N-(cocoalkyl)amidopropyl betaine and sodium lauryl sulfate. Accordingly, the present application also includes a pharmaceutical composition comprising, consisting essentially of or consisting of:

(a) about 1% (w/w) to about 10% (w/w) ibuprofen;
(b) about 25% (w/w) to about 35% (w/w) ethanol;
(c) about 10% (w/w) to about 20% (w/w) propylene glycol;
(d) about 35% (w/w) to about 45% (w/w) water;
(e) about 2% (w/w) to about 5% (w/w) triethyl citrate;
(f) about 0.5% (w/w) to about 2.5% (w/w) lactic acid;
(g) about 1% (w/w) to about 3% (w/w) sodium lauryl sulfate; and
(h) about 2% (w/w) to about 10% (w/w) N-(cocoalkyl)amidopropyl betaine.

In another embodiment of the present application, there is included a pharmaceutical composition comprising, consisting essentially of or consisting of ibuprofen, ethanol, water, triethyl citrate, lactic acid, transcutol, propylene glycol and N-(cocoalkyl)amidopropyl betaine. Accordingly, the present application also includes a pharmaceutical composition comprising, consisting essentially of or consisting of:

(a) about 1% (w/w) to about 10% (w/w) ibuprofen;
(b) about 25% (w/w) to about 35% (w/w) ethanol;
(c) about 15% (w/w) to about 25% (w/w) transcutol;
(d) about 1% (w/w) to about 10% (w/w) propylene glycol;
(e) about 25% (w/w) to about 35% (w/w) water;
(f) about 2% (w/w) to about 5% (w/w) triethyl citrate;
(g) about 0.5% (w/w) to about 2.5% (w/w) lactic acid; and (i) about 2% (w/w) to about 10% (w/w) N-(cocoalkyl) amidopropyl betaine.

In another embodiment of the present application, there is included a pharmaceutical composition comprising, consisting essentially of or consisting of ibuprofen, ethanol, water, triethyl citrate, lactic acid, DMSO and N-(cocoalkyl)amidopropyl betaine. Accordingly, the present application also includes a pharmaceutical composition comprising, consisting essentially of or consisting of:
- (a) about 1% (w/w) to about 10% (w/w) ibuprofen;
- (b) about 30% (w/w) to about 40% (w/w) ethanol;
- (c) about 35% (w/w) to about 45% (w/w) water;
- (d) about 2% (w/w) to about 5% (w/w) triethyl citrate;
- (e) about 0.5% (w/w) to about 2.5% (w/w) lactic acid;
- (f) about 2% (w/w) to about 10% (w/w) N-(cocoalkyl) amidopropyl betaine; and
- (g) about 5% (w/w) to about 15% (w/w) DMSO.

In another embodiment of the present application, the water component of the hydroalcoholic chassis is buffered and, is optionally adjusted with a pH adjusting agent to a pH of about 6.5. Accordingly, there is included in the present application, a pharmaceutical composition comprising, consisting essentially of or consisting of ibuprofen, ethanol, phosphate buffered saline (PBS), triethyl citrate, lactic acid, propylene glycol, amphosol and transcutol, wherein the pH is adjusted to about 6.5. In an embodiment, the present application includes a pharmaceutical composition comprising, consisting essentially of or consisting of:
- (a) about 1% (w/w) to about 10% (w/w) ibuprofen;
- (b) about 25% (w/w) to about 35% (w/w) ethanol;
- (c) about 15% (w/w) to about 25% (w/w) transcutol;
- (d) about 1% (w/w) to about 10% (w/w) propylene glycol;
- (e) about 25% (w/w) to about 35% (w/w) PBS;
- (f) about 1% (w/w) to about 5% (w/w) triethyl citrate;
- (g) about 0.5% (w/w) to about 2.5% (w/w) lactic acid; and
- (i) about 2% (w/w) to about 10% (w/w) amphosol,
wherein the pH is adjusted to about 6.5

In a further embodiment of the present application all compositions additionally comprise a cellulosic thickening agent, for example HPC, in an amount of about 0.5% (w/w) to about 5.0% (w/w), about 0.5% (w/w) to about 3.0% (w/w), about 0.5% (w/w) to about 2.0% (w/w), or about 1.5% (w/w) to about 2.5% (w/w).

In a further embodiment of the present application all compositions additionally comprise at least one preservative, for example methyl paraben and/or propyl paraben, in an amount of about 0.1% (w/w) to about 5.0% (w/w), about 0.1% (w/w) to about 3.0% (w/w) or about 0.1% (w/w) to about 1.0% (w/w).

III. Methods of Preparation

In embodiments of the present application, the pharmaceutical compositions are formulated as a spray, cream, an emulsion, a microemulsion, a gel (e.g., a hydrogel, an organogel, an inorganic or silica gel, a high-viscosity gel or a low-viscosity gel), a lotion, a lacquer, an ointment, a solution (e.g., a moderate to highly viscous solution), or a transdermal patch. In a suitable embodiment, the composition is a gel, for example, a low-viscosity gel or a spray. Alternatively, the composition is a high-viscosity gel. The pharmaceutical composition of the present application may also be formulated as a transdermal patch. Low viscosity gels are, for example, gels having a dynamic viscosity in the range of about 400-4000 cP at STP. High viscosity gels are, for example, gels having a dynamic viscosity of at least 4000 cP at STP.

Methods of preparing compositions for topical administration are known in the art (see, for example, Remington's Pharmaceutical Sciences, 2000-20th edition, and The United States Pharmacopeia: The National Formulary, USP 24 NF19, published in 1999). In the present application all compositions are based on a hydroalcohilic chassis therefore alcohol-soluble components are dissolved in the alcohol and water soluble components are dissolved in the water and the two solutions, once homogeneous, are slowly mixed to homogeneity.

IV: Methods of Treatment

In certain embodiments, the present application includes a method for treating pain comprising applying an effective amount of a topical ibuprofen composition of the application to a subject in need thereof. In one embodiment, the pharmaceutical composition is applied to the skin of the subject.

Also included in the present application is a use of a topical ibuprofen composition of the application to treat pain as well as a topical ibuprofen composition of the application for use to treat pain.

In another embodiment of the present application, ibuprofen is delivered locally to the skin with minimal systemic absorption. In yet another embodiment, ibuprofen is delivered to and through the skin with minimal systemic absorption. In a still yet another embodiment, ibuprofen is delivered to the tissue surrounding or under the area of skin application with minimal systemic absorption.

In other embodiments, the ibuprofen is delivered to a human or a non-human mammal.

The compositions of the application are useful to alleviate acute pain, chronic pain, or both. Compositions of the application are particularly suited for use in treating acute pain due to minor strains, sprains and contusions. In an embodiment of the application the pain is associated with inflammation. In a further embodiment the pain is associated with osteoarthritis. In another embodiment, the compositions of the present application are useful for the treatment of other chronic joint diseases characterized by joint pain, degeneration of articular cartilage, impaired movement, and stiffness. Suitable joints include, for example, the knee, elbow, hand, wrist and hip. In a further embodiment of the present application, the compositions of the application are useful for the treatment of other pain-associated disorders, including (but not limited to) muscle pain, lower back pain, neck pain, rheumatoid arthritis, tendonitis, fibromyalgia, myofascial pain, Carpal tunnel syndrome, gout and neuropathic pain conditions.

Due to the properties of higher flux and greater in vivo absorption, it is believed that the compositions of the present application can be administered at lower dosing (i.e. less frequent) than previously described ibuprofen formulations having the same concentration. In particular, it is expected that the compositions of the application can be used at three times a day dosing, twice a day dosing or once a day dosing.

Compositions of the present application may, if desired, be presented in a bottle, jar, sachet, or other container-closure system approved by government regulatory agencies, which may contain one or more unit dosage forms containing the active ingredient.

In some aspects, the compositions of the present invention are dispensed from a reservoir using a release assembly (e.g., a pump head) to dispense an amount of the composition whenever the release assembly is put into action. The enclosure may, for example, comprise an airless pump bottle with a pump head. The amount of the composition dispensed by the pump may or may not be metered to dispense a consistent amount of formulation.

The package or dispenser may also be accompanied by a notice associated with the container in a form prescribed by a governmental agency regulating the manufacture, use, or sale of pharmaceuticals, the notice indicating approval by the agency.

The following non-limiting examples are illustrative of the present application:

V. Examples

Materials

All materials used in the formulations of the present application were from commercial sources. Ibuprofen, USP was obtained from Spectrum Chemicals and Laboratory Products (New Brunswick, N.J., USA) or Arch Pharmalabs (India). Ibuprofen from Arch Pharmalabs had a smaller average crystallite size and hence faster dissolution characteristics. Transcutol was obtained from Gattefosse Corporation, Paramus, N.J., USA. Triethyl citrate (FCC grade) was obtained from Spectrum Chemicals and Laboratory Products, New Brunswick, N.J., USA. DMSO was obtained from Gaylord Chemical Corporation, Slidell, La., USA. D-Panthenol and poloxamer 188 (Lutrol™ F 68) were obtained from BASF, Ludwigshafen, Germany. α-Terpineol was obtained from Alpha Aesar. Amphosol HCG was obtained from Stepan Company (Chicago, Ill.). Softigen™ was obtained from Sasol (Huls) America (Houston, Tex.). Glyceryl Monoricinoleate (GR) was obtained from Phoenix Chemical, Somerville, N.J., USA. Propylene glycol was obtained from Riedel De Haen. D,L-Lactic acid was obtained from Mallinckrodt. Hydroxypropyl cellulose HY121 was obtained from Spetrum. Water was obtained from Thermo Scientific. All remaining chemicals were obtained from VWR, West Chester, Pa., USA, or Sigma Aldrich, St. Louis, Mo., USA. Ibugel™ was obtained from Dermal Laboratories, UK. Unless otherwise specified, the percentage specified is a weight/weight percentage.

Example 1

General Procedure for Formulation Preparation

For a typical composition of the present application, the ibuprofen was weighed into a suitable container and the alcohol, triethyl citrate and other solvents or agents were transferred quantitatively into the container and the resulting mixture was stirred using a suitable mixer until dissolution was complete. Lactic acid, was then added and mixing was continued. Water was then weighed into a separate container and the surfactants were added to the water and the resulting mixture was mixed until dissolution was complete. The aqueous surfactant portion was then added slowly to the alcohol portion and mixing was continued until dissolution was complete. Excessive stirring was avoided to prevent foaming.

The following representative formulations were prepared (refer to Table 1 for specific amounts of the components):
(a) Preparation of Ibuprofen Formulation (IB 449)
 1—Weigh Ibuprofen in a suitable container.
 2—Quantitatively transfer ethanol, triethyl citrate, transcutol, and propylene glycol. Using a suitable mixer, mix until complete dissolution.
 3—Add lactic acid and mix well.
 4—In separate container weigh water and add sodium lauryl sulfate. Mix until complete dissolution.
 5—Slowly add item from step 4 to item from step 3. Mix until complete dissolution. Avoid excessive stirring to prevent foaming.
(b) Preparation of Ibuprofen Formulations (IB 449a and 449b)
 1—Weigh Ibuprofen in a suitable container.
 2—Quantitatively transfer ethanol, triethyl citrate, transcutol, and propylene glycol. Using a suitable mixer, mix until complete dissolution.
 3—Add lactic acid and mix well.
 4—In separate container weigh water and add sodium lauryl sulfate. Mix until complete dissolution.
 5—Slowly add item from step 4 to item from step 3. Mix until complete dissolution. Avoid excessive stirring to prevent foaming.
(c) Preparation of Ibuprofen Formulation (IB 456)
 1—Weigh Ibuprofen in a suitable container.
 2—Quantitatively transfer ethanol, triethyl citrate and propylene glycol. Using a suitable mixer, mix until complete dissolution.
 3—Add lactic acid and mix well.
 4—In separate container weigh water, add sodium lauryl sulfate and Amphosol. Mix until complete dissolution.
 5—Slowly add item from step 4 to item from step 3. Mix until complete dissolution. Avoid excessive stirring to prevent foaming.
(d) Preparation of Ibuprofen Formulation (IB 486)
 1—Weigh Ibuprofen in a suitable container.
 2—Quantitatively transfer ethanol, triethyl citrate and propylene glycol. Using a suitable mixer, mix until complete dissolution.
 3—Add lactic acid and mix well.
 4—In separate container weigh water, add Amphosol. Mix until complete dissolution.
 5—Slowly add item from step 4 to item from step 3. Mix until complete dissolution. Avoid excessive stirring to prevent foaming.

Other formulations were prepared and representative examples are summarized in Table 1. These formulations can also be prepared using a buffer instead of water. Additionally or alternatively, the pH value of the hydroalcoholic chassis and/or final composition can be adjusted using one or more pH adjusting agents.

Example 2

Exemplary Procedure for Skin Permeation Measurement

The permeation of ibuprofen through porcine skin from each of the present formulations was measured using Franz diffusion cells ("FDC"s). Porcine skin pieces are obtained from Lampire Biological Laboratories, Inc., Pipersville, Pa. Porcine skins were collected immediately following animal sacrifice, and the hairs were trimmed with clippers. Larger pieces of excess fat were removed with a filet knife. The skin was then trimmed to a set thickness of some 2 mm, cut into individual pieces, wrapped in aluminum foil, frozen, shipped, and stored at −78° C.

Prior to use, the skin pieces were allowed to thaw, in air, to room temperature. Before use, the skin was dermatomed to a thickness of 0.5 to 1 mm and cut into circular pieces of an appropriate size prior to mounting in the FDC. The FDCs had a 3-ml receptor well volume, that was filled with isotonic phosphate buffered saline ("PBS") doped with 0.01% sodium azide. The flanges of the FDCs were coated with vacuum grease to ensure a complete seal and were clamped together with uniform pressure using a pinch clamp (SS #18 VWR 80073-350 from VWR Scientific, West Chester Pa.). After the FDCs were assembled, the porcine skin was optionally allowed to pre-hydrate for 45 min with isotonic PBS. Isotonic PBS was then removed and the formulation was applied to the donor well or directly to the skin surface, depending on the amount of formulation applied. The receptor wells were maintained at 37° C. (temperature on the surface of the skin is about 30° C.) in a stirring block with continual agitation via a stir bar.

The flux rates were calculated using the fact that the donor well of each cell had an approximate area of 0.55 cm$^2$. Samples were drawn from the receptor wells at various times, as provided in the examples that follow. Franz diffusion cell measurements were typically made in six-fold replicates for each formulation. The concentrations of ibuprofen in the samples were measured using HPLC analysis using a C18 column and acetonitrile and water as the mobile phase. Generally, in the examples that follow, permeation data were reported by plotting a curve showing the cumulative amount of etoricoxib that permeates across the skin as a function of time. The flux rate can be computed as the time derivative of this curve.

All flux measurements reported herein are for the racemic (R/S) form of ibuprofen. Measurements have revealed no significant difference in flux of the racemic form, compared to the (S) form (the form with substantially higher biological activity), when applied at the same total concentration in the same vehicle. Replacement of the racemic ibuprofen by Dex (S) ibuprofen in any of the formulations described herein is expected to provide a similar flux but about a 2× increase in efficacy [Mayrhofer F. *Efficacy and long-term safety of dexibuprofen [S(+)-ibuprofen]: a short-term efficacy study in patients with osteoarthritis of the hip and a 1-year tolerability study in patients with rheumatic disorders.* Clin Rheumatol. 2001 November; 20 Suppl 1:S22-9; Singer F, Mayrhofer F, Klein G, Hawel R, Kollenz C J. *Evaluation of the efficacy and dose-response relationship of dexibuprofen (S(+)-ibuprofen) in patients with osteoarthritis of the hip and comparison with racemic ibuprofen using the WOMAC osteoarthritis index.* Int J Clin Pharmacol Ther. 2000 January; 38(1):15-24].

As shown in Table 2, compositions of the present application showed three to four times relative enhancement in flux of ibuprofen over a comparative formulation (Ibugel™)

Example 3

Effect of Triethyl Citrate and Surfactants

Several ibuprofen (5% w/w) compositions were prepared without the addition of triethyl citrate and/or surfactants. All compositions prepared without both triethyl citrate and a surfactant showed immediate instability (e.g. precipitation). All compositions prepared without either triethyl citrate or a surfactant showed instability (e.g. precipitation) after 24 hours.

Example 4

Effect of Addition of Thickening Agents

Formulations were prepared using the general procedure described in Example 1 that included 1% hydroxypropyl cellulose (HY121). For example, formulation 449b (Example 1b) comprised 1% HY121 (see FIG. 1 with reference to Table 3 for identification of composition components). As can be seen from the bar graph in FIG. 1, the addition of thickener did not cause a significant effect on the flux of ibuprofen.

Example 5

Effect of Combinations of Alcohols

Figure 2:
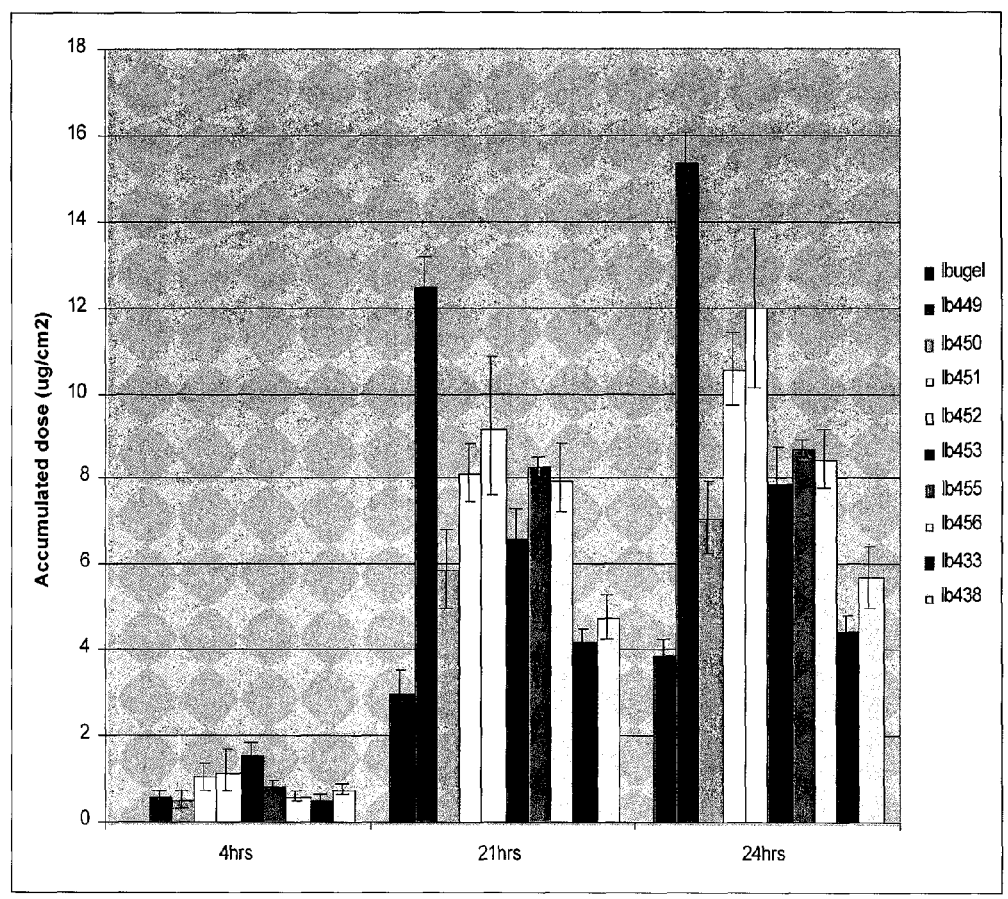
FIG. 2 is a bar graph showing the effect of various combinations of alcohols on the flux of compositions that represent embodiments of the present application. Reference is made to Table 4 for the identity and amounts of the components in the compositions.

Formulations were prepared using the general procedure described in Example 1 that included various combinations of alcohols. As can be seen in FIG. 2 (with reference to Table 4 for identification of composition components) the alcohol combination of 14% transcutol, 10% propylene glycol and 20% ethanol in composition no. Ib449 provided optimum results.

Example 6

Effect of Terpene Addition

Figure 3:
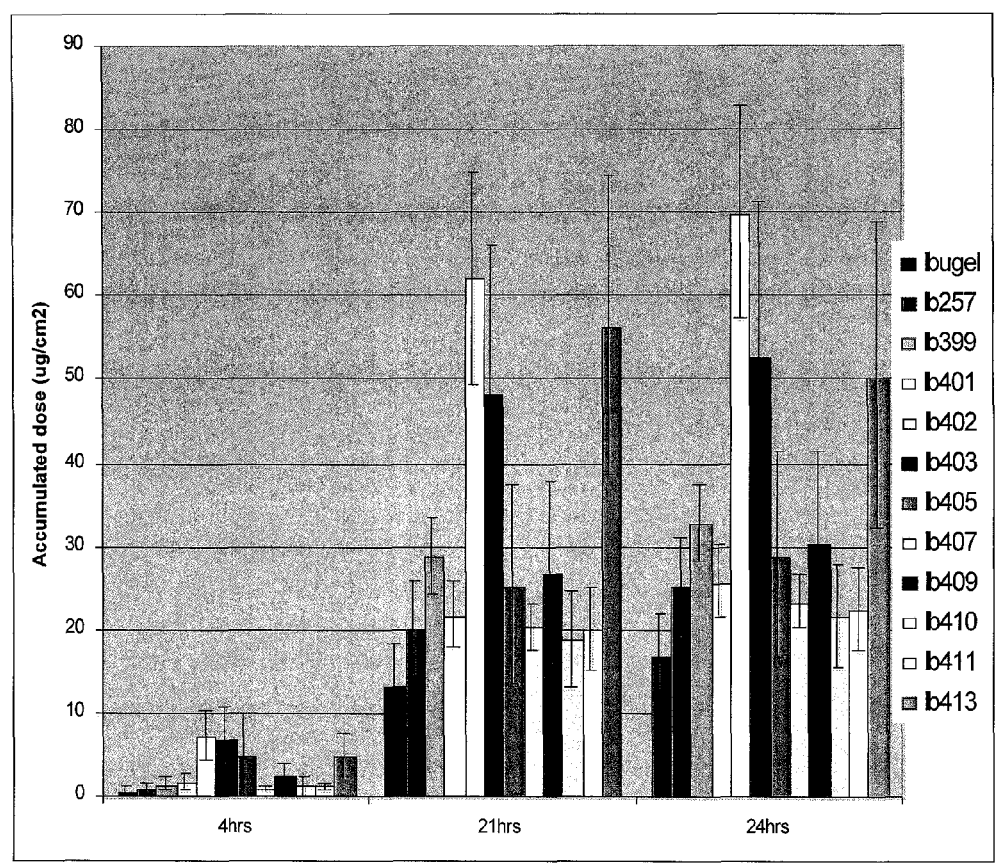
FIG. 3 is a bar graph showing the effect of terpenes on the flux of compositions that represent embodiments of the present application. Reference is made to Table 5 for the identity and amounts of the components in the compositions.

Formulations were prepared using the general procedure described in Example 1 that included various terpenes. As can be seen in FIG. 3 (with reference to Table 5 for identification of composition components) terpene combinations had an enhancing effect on flux in certain compositions (see composition no. Ib402).

Example 7

Effect of Additional Solvents

Figure 4:
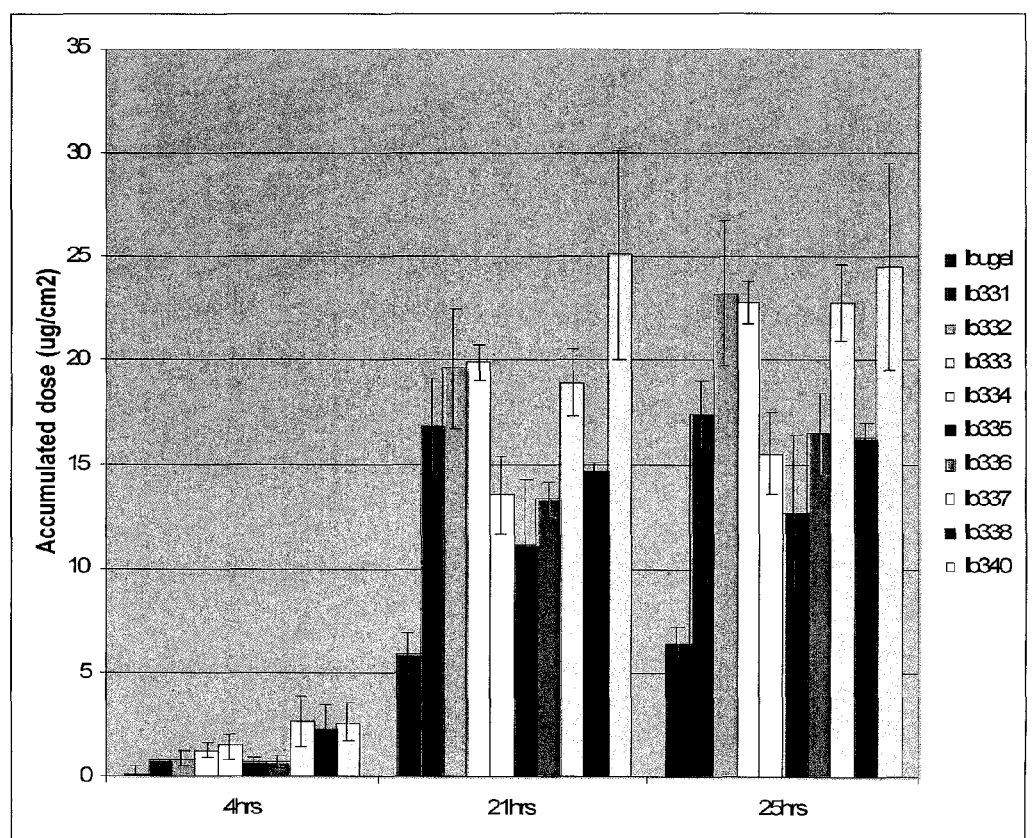
FIG. 4 is a bar graph showing the effect of additional solvents on the flux of compositions that represent embodiments of the present application. Reference is made to Table 6 for the identity and amounts of the components in the compositions.
Figure 5:
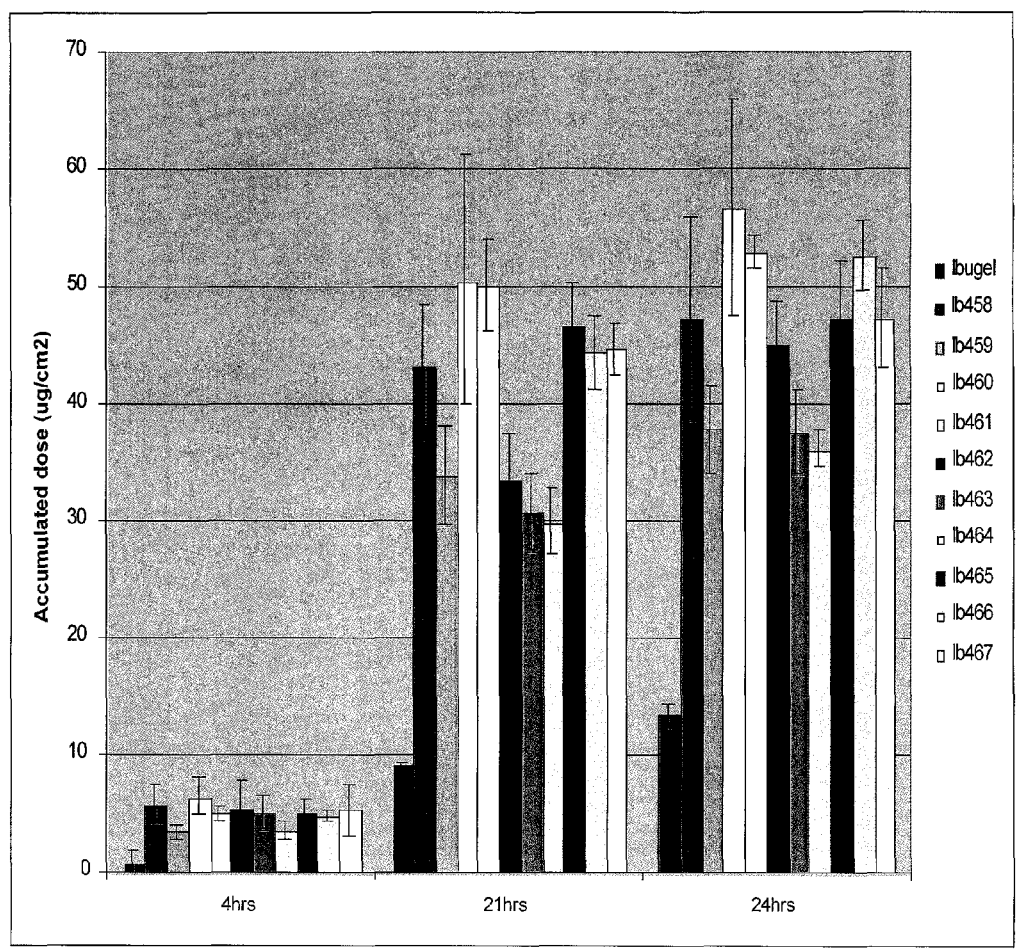
FIG. 5 is a bar graph showing the effect of additional solvents on the flux of compositions that represent embodiments of the present application. Reference is made to Table 7 for the identity and amounts of the components in the compositions.
Figure 6:
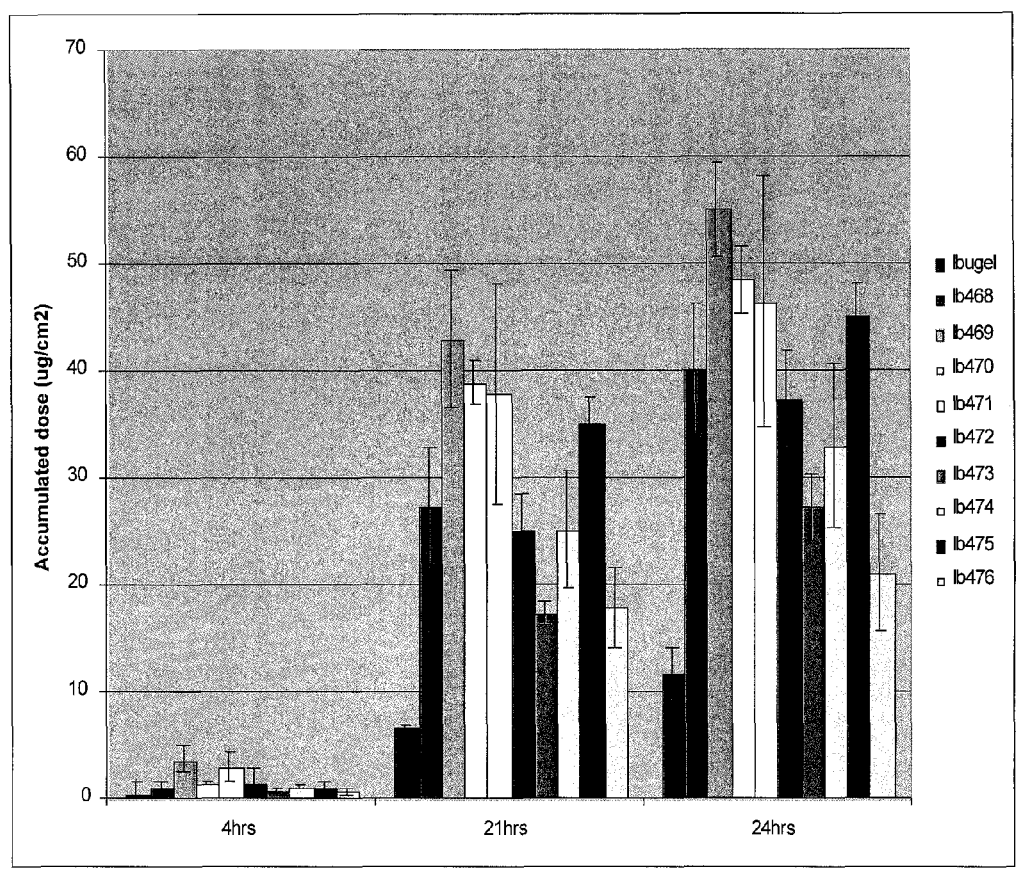
FIG. 6 is a bar graph showing the effect of additional solvents on the flux of compositions that represent embodiments of the present application. Reference is made to Table 8 for the identity and amounts of the components in the compositions.

Formulations were prepared using the general procedure described in Example 1 that included DMSO and/or dimethylacetamide (DMA) as additional solvents. As can be seen in FIG. 4 (with reference to Table 6 for identification of composition components), FIG. 5 (with reference to Table 7 for identification of composition components) and FIG. 6 (with reference to Table 8 for identification of composition components) in certain compositions DMSO alone or in combination with DMA had an optimum effect (see composition nos. Ib332, Ib333, Ib340, Ib460, Ib461, IB469 and Ib470).

Example 8

Thickened Formulation

Formulation (IB949) was prepared based on Formulation No. IB486 (Table 1), using the following procedure. The formulation is presented in Table 9.

Ibuprofen was first dissolved in the organic solvents (ethanol combined with Transcutol), followed by the addition of triethyl citrate, propylene glycol, propyl and methyl parabens, sodium lauryl sulfate, D,L-lactic acid and approximately half of the water. After mixing and dissolving the components, the remainder of the water was added, followed by gradual introduction of the gelling agent. The composition was mixed overnight using a mixer, or until no lumps and undispersed material was evident, if sooner. The process took ~20 hours to be completed. Any air bubbles that formed during the mixing process were found to disappear within ~30 min when the formulation was left to stand at room temperature ("RT").

Example 9

Effect of Modifying Thickened Formulations

Formulations were prepared based on Formulation No. IB949 (Table 9), using the general procedure described in Example 8.

The slate of compositions (Table 10) sampled variations in the amounts of sodium lauryl sulfate, triethyl citrate and lactic acid. Specifically, the levels of sodium lauryl sulfate were varied between 1 and 3%. The amount of lactic acid was varied between 1 and 2%, and the level of triethyl citrate was adjusted between 0.5 and 1.0%. The concentration of water was held constant while the concentration of ethanol was adjusted commensurate with the changes in MPE™ concentrations.

Figure 7:
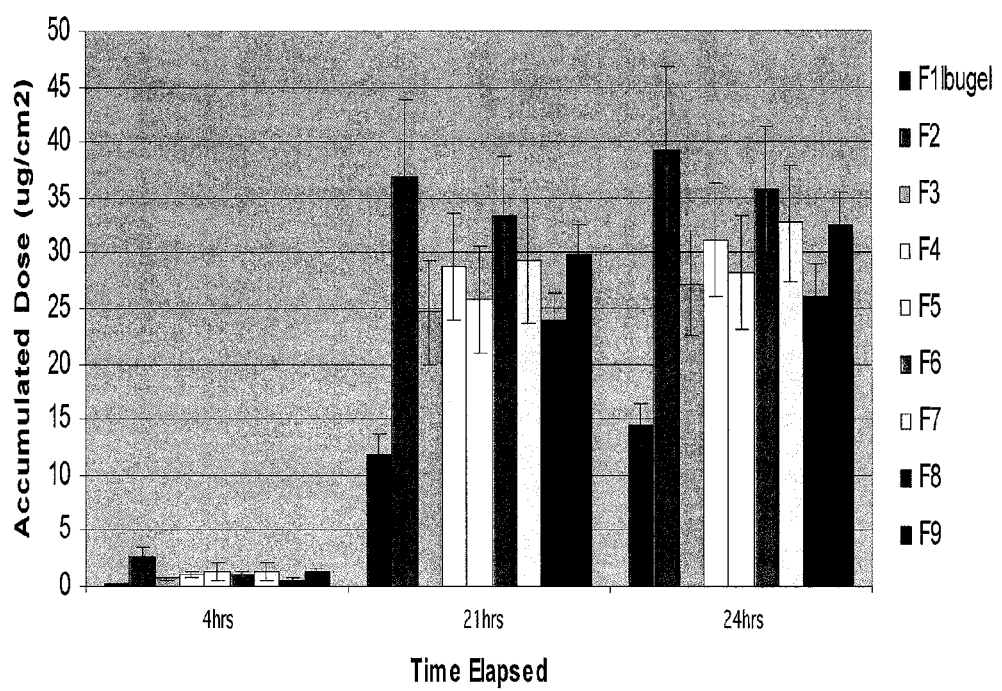
FIG. 7 is a bar graph showing the flux of modified thickened formulations that represent embodiments of the present application. Reference is made to Table 10 for the identity and amounts of the components in the compositions.

Permeation profiles are shown in FIG. 7. The Enhancement Ratio (ER) for the individual formulations is provided at Table 11.

Formulation viscosities were measured at RT using a Brookfield viscometer (spindle #31). The measurements were made within 24 hrs of formulation preparation. Data showing formulation viscosities (centipoise) measured at differing rotation speeds (rotations per minute "rpm") are shown at Table 12.

Results:

Based on the cumulative ibuprofen flux measured in the receptor well fluid at the end of the 24 h study, the following conclusions were reached:

Sodium Lauryl Sulfate:

the optimal concentration of sodium lauryl sulfate is 2%; changing the sodium laurel sulfate concentration from 2% led to a reduction in ibuprofen delivery across the porcine skin (F2 vs F3 and F4);

Lactic Acid:

the optimal concentration of lactic acid appears to be 1.5% (F5, F6, and F7);

Triethyl Citrate:

Based on the present study the optimal concentration of triethyl citrate appears to be 2% since the reduction of triethyl citrate levels to 0.5 and 1.0% led to diminished ibuprofen permeation (F2 vs F8, and F9).

The viscosity data indicated that all formulations have similar viscosities. However, formulation F7 (with 3% lactic acid) shows somewhat higher viscosity values, as shown in Table 12.

Example 10

Effect of pH and Lactic Acid

Figure 8:
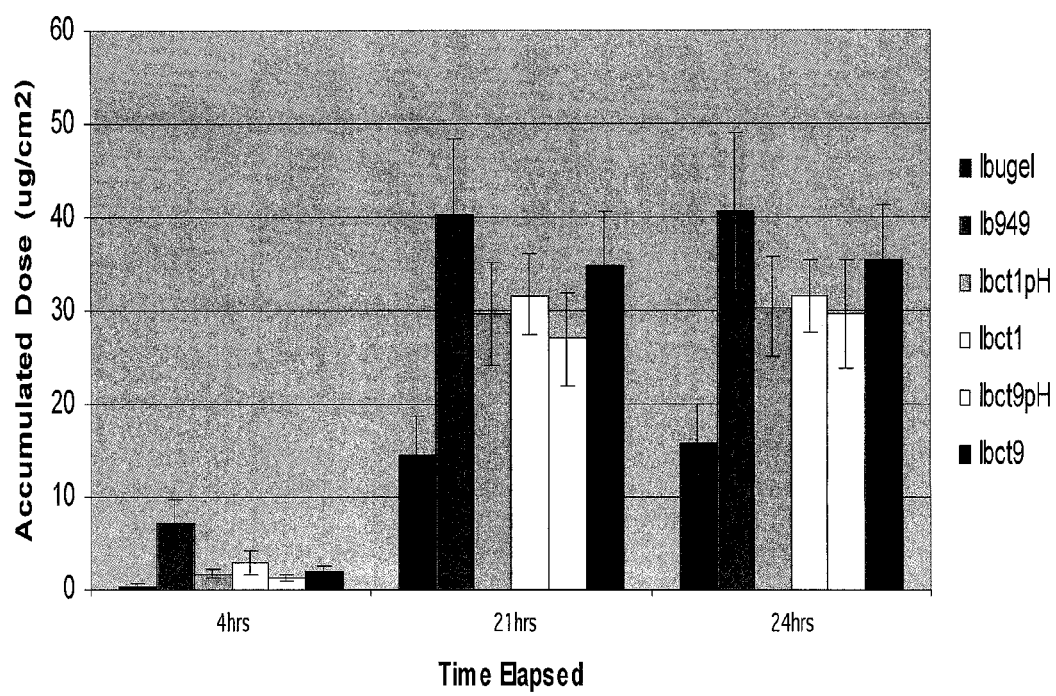
FIG. 8 is a bar graph showing the effect of pH on the flux of compositions that represent embodiments of the present application. Reference is made to Table 12 for the identity and amounts of the components in the compositions.
Figure 9:
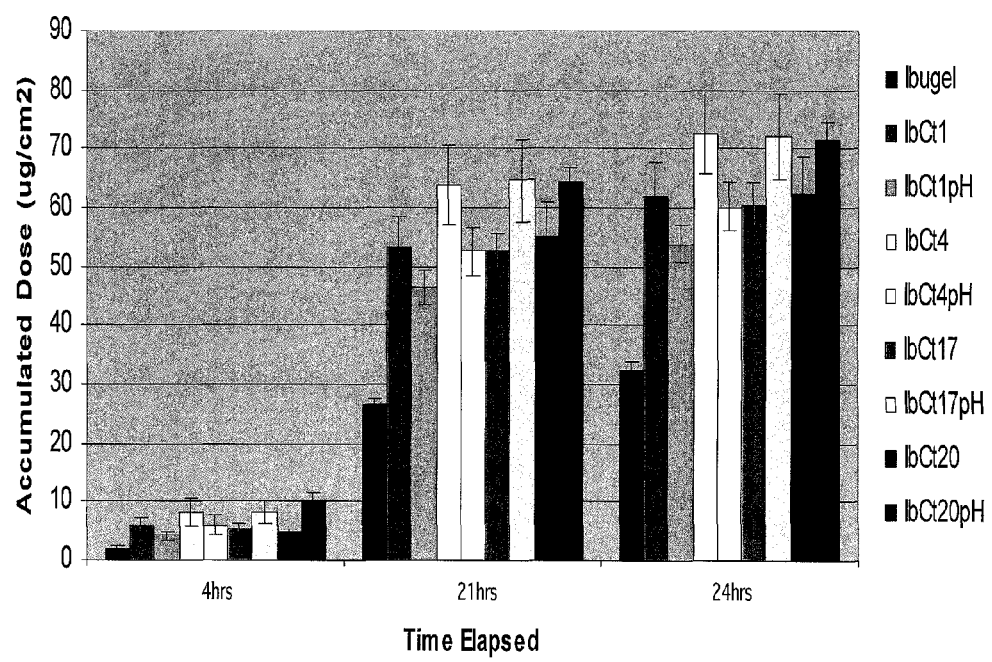
FIG. 9 is a bar graph showing the effect of lactic acid levels in citrate buffer on the flux of compositions that represent embodiments of the present application. Reference is made to Table 13 for the identity and amounts of the components in the compositions.

These studies were conducted to evaluate the role of pH on ibuprofen permeation and the effect of lactic acid concentration on citrate buffer levels. As can be seen in FIG. 8 (with reference to Table 13 for identification of composition components) the permeation of ibuprofen was not significantly affected by pH. Similarly, in FIG. 9 (with reference to Table 14 for identification of composition components) the permeation of ibuprofen was not significantly affected by the level of lactic acid on citrate buffer.

Example 11

Effect of Buffers

Figure 10:
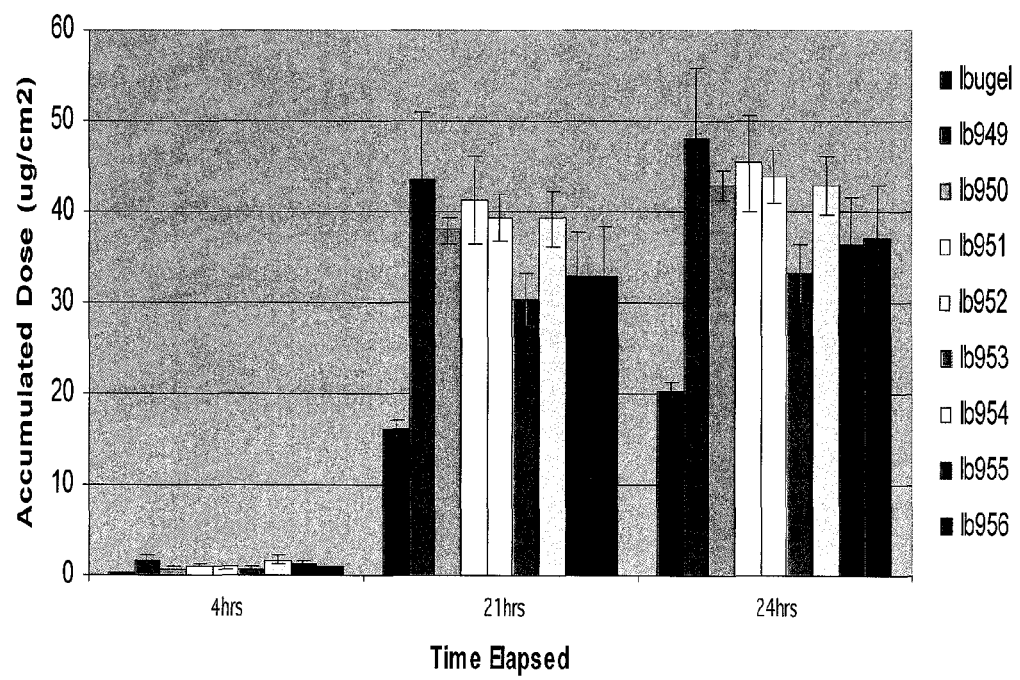
FIG. 10 is a bar graph showing the flux of compositions that have not been pH adjusted that represent embodiments of the present application. Reference is made to Table 15 for the identity and amounts of the components in the compositions.
Figure 11:
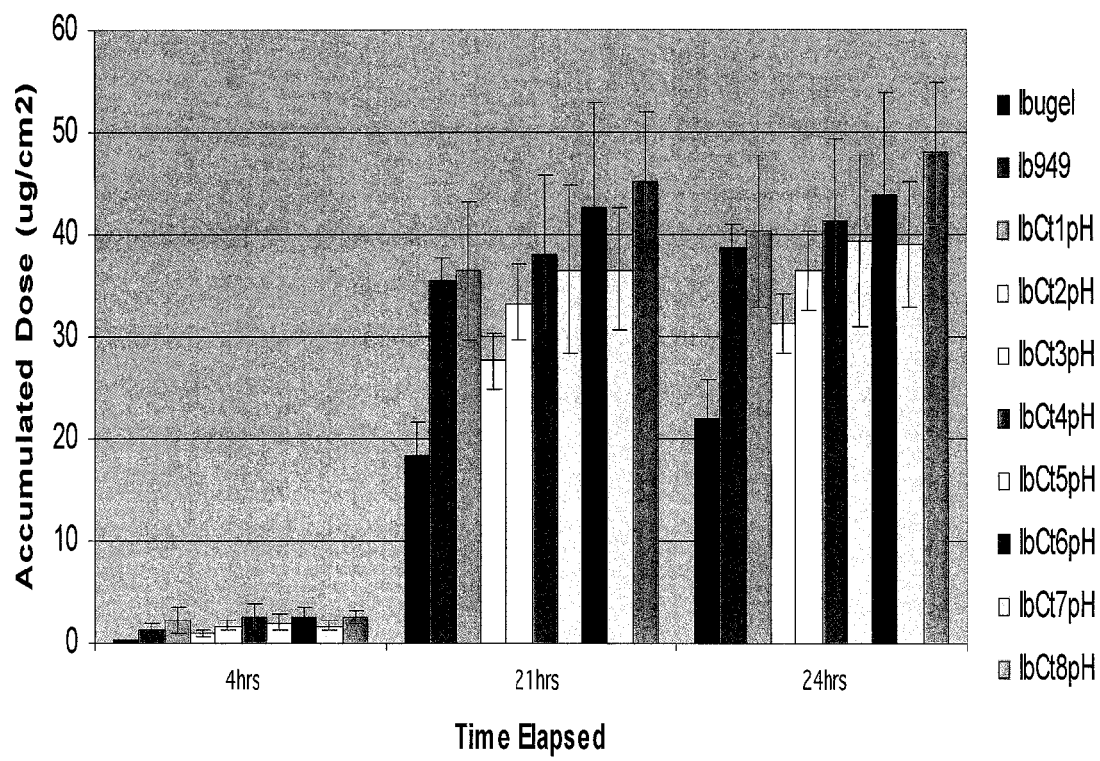
FIG. 11 is a bar graph showing the effect of buffer-adjusted pH (~pH 4.2) on the flux of compositions that represent embodiments of the present application. Reference is made to Table 16 for the identity and amounts of the components in the compositions.
Figure 12:
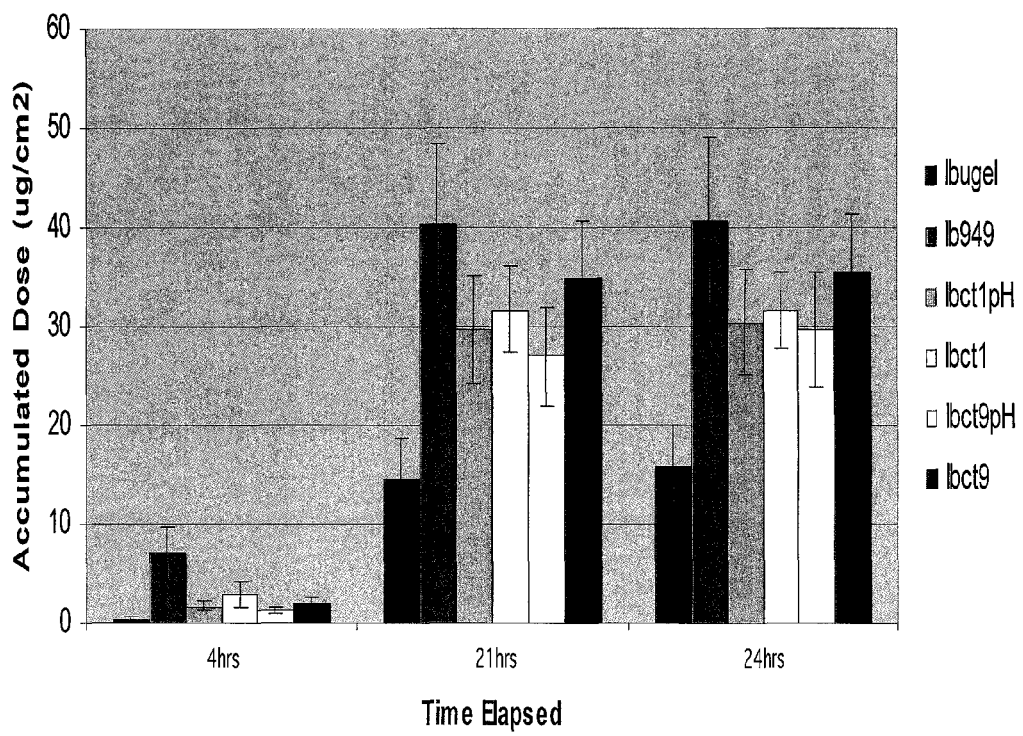
FIG. 12 is a bar graph showing the effect of pH and buffers on the flux of compositions that represent embodiments of the present application. Reference is made to Table 17 for the identity and amounts of the components in the compositions.

Formulations were prepared using the general procedure described in Example 1 or 8. The effect of including a buffer in the formulation was measured in this study. The viscosity and pH of ingredient-modified formulations was also evaluated. As can be seen in FIGS. 10, 11 and 12 (with reference to Tables 15, 16 and 17, respectively, for identification of composition components) replacement of water by buffer, with or without final pH adjustment, did not significantly affect permeation behavior.

Tables 18 and 19 show the effect of removing ingredients on viscosity, while the effect of ingredients on pH are shown in Table 20. The removal of ingredients caused, to a certain degree, a shift in pH and change in viscosity of the final formulations.

Example 12

Effect of Varying Ingredient Concentration in Thickened Formulations

Formulations were prepared using the general procedure described in Example 8 and were based on IB949 with 2% HY 121 as thickener. In particular, the percentage of sodium lauryl sulphate was varied from 1-3%, the percentage of lactic acid was varied from 0.5-1.5% and the percentage of triethyl citrate was varied from 0.5-1%. In further studies, triethyl citrate was substituted with other esters. pH and viscosities of the formulations were measured and are provided at Table 22.

Figure 13:
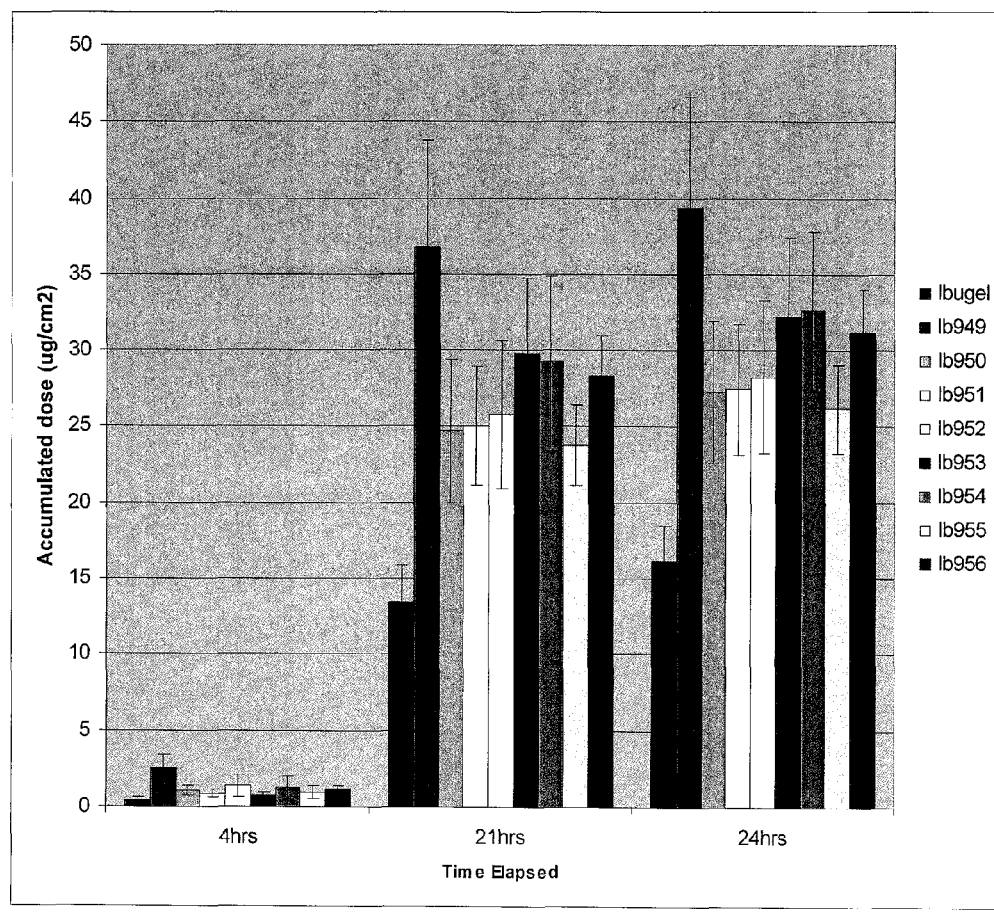
FIG. 13 is a bar graph showing the effect of percent ingredients on the flux of compositions that represent embodiments of the present application. Reference is made to Table 21 for the identity and amounts of the components in the compositions.

As can be seen in FIG. 13 (with reference to Table 21 for identification of composition components) an increase or decrease of sodium lauryl sulphate reduced permeation of ibuprofen. Similarly, a change in lactic acid or triethyl citrate caused a drop in permeation. Substituting triethyl citrate with other esters, such as diisoproply adipate, diethyl sebacate, ethyl oleate, isopropyl myristate and isopropyl palmitate, did not improve results.

Example 13

Optimized Formulation

An optimized formulation was prepared based on Formulation No. IB486 (Table 1), using the general procedure described in Example 1. The formulation is prepared in a PBS buffered system with a final pH adjusted to ~6.5. The formulation is shown at Table 23.

Example 14

General Method for Skin Retention Studies

At the end of the permeation study, skin samples can be removed from the Franz cells for skin retention studies. Any excess of formulation is carefully wiped away, first with cotton swabs and then with lint-free paper. The skin samples are quickly washed with cold water and ethanol, and the skin samples are then dried for 1 h at room temperature. After being cut into small pieces with a pair of stainless steel scissors, the samples are transferred into 5 mL scintillation vials, and 2 mL of absolute ethanol is added. The samples are allowed to incubate for 24 h at room temperature. The liquid phase is then filtered through 9 mm diameter disposable syringe filters (0.45 µm, Acrodisc®). The filtrate, after appropriate dilution, is assayed by HPLC.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Ingredients | \multicolumn{11}{c}{Formulation name IB} |
|---|---|---|---|---|---|---|---|---|---|---|---|
| | 257 wt/wt % | 229 wt/wt % | 340 wt/wt % | 402 wt/wt % | 332 wt/wt % | 333 wt/wt % | 391 wt/wt % | 426 wt/wt % | 413 wt/wt % | 427 wt/wt % | 449 wt/wt % |
| Softigen | | | | | | | 3 | | | | |
| Triethyl Citrate | 3 | 4.5 | 3 | 3 | 4.5 | 3 | | 4.5 | 3 | 4.5 | 3 |
| Amphosol | | 7.5 | 7.5 | | 7.5 | 7.5 | 7.5 | 7.5 | | 7.5 | |
| NA Lauryl Sulphate | 2 | 2 | 2 | 2 | | | 2 | | 2 | | 2 |
| DMSO | | | 10 | | 10 | 10 | | | | | |
| Ethanol | 44 | 34 | 29 | 44 | 34 | 34 | | 15 | 34 | 44 | 34 | 20 |
| Water | 44.5 | 47.5 | 39 | 40 | 37.5 | 39 | 33 | 44 | 38 | 41 | 44.5 |
| Lactic Acid | 1.5 | 1.5 | 1.5 | 1 | 1.5 | 1.5 | 1 | | | | 1.5 |
| Ibuprofen | 5 | 5 | 5 | 5 | 5 | 5 | 5 | 5 | 5 | 5 | 5 |
| Poloxamer 188 | | | | | | | | 5 | | | |
| Dimethyl-acetamide | | | 5 | | | | | | | | |
| Limonene | | | | | | | | 5 | | | |
| α-Terpineol | | | | 5 | | | | 5 | 5 | 5 | |
| GL | | | | | | | | | | 3 | |
| Transcutol | | | | | | | 10 | | | | 14 |
| GR | | | | | | | | | 3 | | |
| IPM | | | | | | | 3 | | | | |
| Tween 80 | | | | | | | 10 | | | | |
| PG | | | | | | | 10 | | | | 10 |
| Isopropanol | | | | | | | | | | | |
| HY 117 | | | | | | | | | | | |
| HY 121 | | | | | | | | | | | |
| Urea | | | | | | | | | | | |
| D-Panthenol | | | | | | | | | | | |

| Ingredients | \multicolumn{10}{c}{Formulation name IB} |
|---|---|---|---|---|---|---|---|---|---|---|
| | 449a wt/wt % | 449b wt/wt % | 456 wt/wt % | 460 wt/wt % | 461 wt/wt % | 469 wt/wt % | 470 wt/wt % | 486 wt/wt % | 593 wt/wt % | 594 wt/wt % |
| Softigen | | | | | | | | | | |
| Triethyl Citrate | 3 | 3 | 3 | 3 | 3 | 3 | 2 | 3 | 3 | 3 |
| Amphosol | | | 4 | 5 | 7.5 | 7.5 | 7.5 | 5 | 7.5 | 5 |
| NA Lauryl Sulphate | 2 | 2 | 1 | | | | | | | |
| DMSO | | | | 5 | 10 | 10 | 10 | | | |
| Ethanol | 20 | 20 | 30 | 34 | 29 | 34 | 34 | 30 | 30 | 30 |
| Water | 43.5 | 43.5 | 41.5 | 41.5 | 39 | 40 | 39 | 31.5 | 19 | 21.5 |
| Lactic Acid | 1.5 | 1.5 | 1.5 | 1.5 | 1.5 | 1 | 1.5 | 1.5 | 1.5 | 1.5 |
| Ibuprofen | 5 | 5 | 5 | 5 | 5 | 5 | 5 | 5 | 5 | 5 |
| Poloxamer 188 | | | | | | | | | | |
| Dimethyl-acetamide | | | | | | | | | | |
| Limonene | | | | | | | | | | |
| α-Terpineol | | | | | | | | | | |
| GL | | | | | | | | | | |
| Transcutol | 14 | 14 | | | | | | 20 | 14 | 14 |
| GR | | | | | | | | | | |
| IPM | | | | | | | | | | |
| Tween 80 | | | | | | | | | | |
| PG | 10 | 10 | 14 | | 5 | | | 4 | 10 | 10 |
| Isopropanol | | | | 5 | | | | | | |
| HY 117 | 1 | | | | | | | | | |
| HY 121 | | 1 | | | | | | | | |
| Urea | | | | | | | | | 5 | 5 |
| D-Panthenol | | | | | | | | | 5 | 5 |

GL—Glycerin monolaurate
GR—Glycerin monoricinoleate
IPM—Isopropyl myristate
PG—Proplyene glycol
HY 117—Hydroxy propyl cellulose
HY 121—Hydroxy propyl cellulose NF

TABLE 2

| Formulation name | Relative enhancement in flux |
|---|---|
| 229 | 3.4 |
| 257 | 3.8 |
| 332 | 3.3 |
| 333 | 2.5 |
| 391 | 3.5-3.8 |
| 402 | 3.8 |
| 413 | 2.8 |
| 426 | 3.8 |
| 427 | 3.44 |
| 449 | 3.0-4.0 |
| 449a | 2.0 |
| 449b | 2.0-3.1 |
| 456 | 3.7-3.9 |
| 460 | 3.7-3.9 |
| 461 | 3.7 |
| 469 | 3.5-3.7 |
| 470 | 3.4 |
| 486 | 3.3-3.7 |
| 592 | 2.9-3.2 |
| 593 | 3.4-3.8 |
| 594 | 3.2-3.4 |

TABLE 3

| | Formulation name | | | | | | | | | |
|---|---|---|---|---|---|---|---|---|---|---|
| | Ibugel | Ib449 | Ib449a | Ib449b | Ib445 | Ib445a | Ib445b | Ib4520 | Ib520a | Ib520b |
| Dosing (μl) | 3 | 3 | 3 | 3 | 3 | 3 | 3 | 3 | 3 | 3 |
| Ingredients | wt/wt % | wt/wt % | wt/wt % | wt/wt % | wt/wt % | wt/wt % | wt/wt % | wt/wt % | wt./wt % | wt/wt % |
| Ibuprofen | 5 | 5 | 5 | 5 | 5 | 5 | 5 | 5 | 5 | 5 |
| Transcutol | | 14 | 14 | 14 | | | | | | |
| Isopropanol | | | | | | | | | | |
| PG | | 10 | 10 | 10 | | | | 14 | 14 | 14 |
| Triethyl Citrate | | 2 | 2 | 2 | 1 | 1 | 1 | 3 | 3 | 3 |
| Amphosol | | | | | | | | | | |
| Na Lauryl Sulphate | | 2 | 2 | 2 | 2 | 2 | 2 | 2 | 2 | 2 |
| Ethanol | | 20 | 20 | 20 | 44 | 44 | 44 | 30 | 30 | 30 |
| Urea | | | | | | | | | | |
| Water | | 44.5 | 44.5 | 44.5 | 46.5 | 46.5 | 46.5 | | | |
| Lactic Acid | | 1.5 | 1.5 | 1.5 | 1.5 | 1.5 | 1.5 | | | |
| Tween 20 | | | | | | | | 1 | 1 | 1 |
| Saline phosphate | | | | | | | | 45 | 45 | 45 |
| Thickener Wt % added | | | HY1171 | HY1211 | | HY1171 | HY1211 | | HY1171 | HY1211 |

TABLE 4

| | Formulation name | | | | | | | | | |
|---|---|---|---|---|---|---|---|---|---|---|
| | Ibugel | Ib449 | Ib450 | Ib451 | Ib452 | Ib453 | Ib455 | Ib456 | Ib433 | Ib438 |
| Dosing (μl) | 3 | 3 | 3 | 3 | 3 | 3 | 3 | 3 | 3 | 3 |
| Ingredients | wt/wt % | wt/wt % | wt/wt % | wt/wt % | wt/wt % | wt/wt % | wt/wt % | wt/wt % | wt/wt % | wt/wt % |
| Ibuprofen | 5 | 5 | 5 | 5 | 5 | 5 | 5 | 5 | 5 | 5 |
| Transcutol | | 14 | | 14 | | 10 | 15 | | | |
| Isopropanol | | | 14 | | 14 | 14 | | | | |
| PG | | 10 | | | 10 | | | 14 | | |
| Tween 80 | | | | | | | | | | 2 |
| Triethyl Citrate | | 3 | 3 | 3 | 3 | 3 | 3 | 3 | 3 | |
| Amphosol | | | | | | | 4 | 4 | | |
| Na Lauryl Sulphate | | 2 | 2 | 2 | 2 | 2 | 1 | 1 | | |
| Ethanol | | 20 | 30 | 20 | 20 | 20 | 30 | 30 | 44 | 44 |
| Cetrimonium Bromide | | | | | | | | | 2 | |
| Water | | 44.5 | 44.5 | 44.5 | 44.5 | 44.5 | 40.5 | 41.5 | 45 | 44 |
| Lactic Acid | | 1.5 | 1.5 | 1.5 | 1.5 | 1.5 | 1.5 | 1.5 | 1 | |
| Terpineol | | | | | | | | | | 5 |

TABLE 5

| | Formulation name | | | | | | | | | | | |
|---|---|---|---|---|---|---|---|---|---|---|---|---|
| | Ibugel | Ib257 | Ib399 | Ib401 | Ib402 | Ib403 | Ib405 | Ib407 | Ib409 | Ib410 | Ib411 | Ib413 |
| Dosing (μl) | 3 | 3 | 3 | 3 | 3 | 3 | 3 | 3 | 3 | 3 | 3 | 3 |
| Ingredients | wt/wt % | wt/wt % | wt/wt % | wt/wt % | wt/wt % | wt/wt % | wt/wt % | wt/wt % | wt/wt % | wt/wt % | wt/wt % | wt/wt % |
| Ibuprofen | 5 | 5 | 5 | 5 | 5 | 5 | 5 | 5 | 5 | 5 | 5 | 5 |
| Triethyl Citrate | | 3 | 3 | 3 | 3 | 3 | 3 | 3 | 3 | 3 | 3 | 3 |
| Amphosol | | | | | | | | | | | | |
| Na Lauryl Sulphate | | 2 | 2 | 2 | 2 | 2 | 2 | 2 | 2 | 2 | 2 | 2 |
| DMSO | | | | | | | | | | | | |
| Ethanol | | 44 | 44 | 44 | 44 | 44 | 44 | 44 | 44 | 44 | 44 | 44 |
| Water | | 44.5 | 37 | 37 | 40 | 37 | 37 | 38 | 38 | 41 | 38 | 38 |
| Lactic Acid | | 1.5 | 1 | 1 | 1 | 1 | 1 | | | | | |
| Limonene | | | 5 | 5 | | | | 5 | 5 | | | |
| Terpineol | | | | | 5 | | 5 | | | 5 | 5 | 5 |
| GL | | | 3 | | | | | 3 | | | 3 | |
| GR | | | | 3 | | 3 | | | 3 | | | 3 |

TABLE 6

| | Formulation name | | | | | | | | | |
|---|---|---|---|---|---|---|---|---|---|---|
| | Ibugel | Ib331 | Ib332 | Ib333 | Ib334 | Ib335 | Ib336 | Ib337 | Ib338 | Ib340 |
| | | | | | | Specs | | | | |
| Dosing (μl) | 3 | 3 | 3 | 3 | 3 | 3 | 3 | layers 3 | gel 3 | gel 3 |
| Ingredients | wt/wt % | wt/wt % | wt/wt % | wt/wt % | wt/wt % | wt/wt % | wt/wt % | wt/wt % | wt/wt % | wt/wt % |
| Ibuprofen | 5 | 5 | 5 | 5 | 5 | 5 | 5 | 5 | 5 | 5 |
| Na Docusate | | | | | | | | | | |
| Triethyl Citrate | | 4.5 | 4.5 | 3 | 4.5 | 4.5 | 3 | 4.5 | 4.5 | 3 |
| PG | | | | | | | | | | |
| Lactic Acid | | 1.5 | 1.5 | 1.5 | 1.5 | 1.5 | 1.5 | 1.5 | 1.5 | 1.5 |
| Amphosol | | | 7.5 | 7.5 | | 7.5 | 7.5 | | 7.5 | 7.5 |
| Dimethyl-acetamide | | | | | 5 | 5 | 5 | 5 | 5 | 5 |
| SNLS | | | | | | | | | | |
| Ethanol | | 34 | 34 | 34 | 34 | 34 | 34 | 34 | 24 | 29 |
| Water | | 45 | 37.5 | 39 | 50 | 42.5 | 44 | 45 | 47.5 | 39 |
| DMSO | | 10 | 10 | 10 | | | | 5 | 5 | 10 |

TABLE 7

| | Formulation name | | | | | | | | | |
|---|---|---|---|---|---|---|---|---|---|---|
| | Ibugel | Ib458 | Ib459 | Ib460 | Ib461 | Ib462 | Ib463 | Ib464 | Ib465 | Ib466 | Ib467 |
| | | | | | | Dosing (μl) | | | | | |
| Ingredients | 3 wt/wt % | 3 wt/wt % | 3 wt/wt % | 3 wt/wt % | 3 wt/wt % | 3 wt/wt % | 3 wt/wt % | 3 wt/wt % | 3 wt/wt % | 3 wt/wt % | 3 wt/wt % |
| Ibuprofen | 5 | 5 | 5 | 5 | 5 | 5 | 5 | 5 | 5 | 5 | 5 |
| Triethyl Citrate | | 3 | 3 | 3 | 3 | 3 | 3 | 3 | 3 | 3 | |
| Amphosol | | 7.5 | 7.5 | 5 | 7.5 | 7.5 | 7.5 | 7.5 | 7.5 | 5 | 7.5 |
| Na Lauryl Sulphate | | | | | | | | | | | |
| DMSO | | 10 | 10 | 5 | 10 | 5 | 5 | 5 | 10 | 10 | 10 |
| Ethanol | | 29 | 34 | 34 | 29 | 34 | 34 | 34 | 34 | 34 | 34 |
| Isopropanol | | | | 5 | | | 5 | | | | |
| PG | | | | | 5 | 5 | | | | | |
| Transcutol | | | | | | | | 5 | 5 | | |
| Water | | 44 | 40.5 | 41.5 | 39 | 39 | 39 | 39 | 34 | 41.5 | 42 |
| Lactic Acid | | | 1.5 | | 1.5 | 1.5 | 1.5 | 1.5 | 1.5 | 1.5 | 1.5 |

TABLE 8

| Ingredients | Ibugel | Ib468 | Ib469 | Ib470 | Ib471 | Ib472 | Ib473 | Ib474 | Ib475 | Ib476 |
|---|---|---|---|---|---|---|---|---|---|---|
| Dosing (μl) | 3 wt/wt % | 3 wt/wt % | 3 wt/wt % | 3 wt/wt % | 3 wt/wt % | 3 wt/wt % | 3 wt/wt % | 3 wt/wt % | 3 wt/wt % | 3 wt/wt % |
| Ibuprofen | 5 | 5 | 5 | 5 | 5 | 5 | 5 | 5 | 5 | 5 |
| Triethyl Citrate | | 3 | 3 | 2 | 3 | 3 | 3 | 3 | 3 | 3 |
| Amphosol Na Lauryl Sulphate | | 7.5 | 7.5 | 7.5 | 7.5 | 7.5 | 7.5 | 7.5 | 7.5 | 5 |
| DMSO | | | 10 | 10 | | | | | | |
| Ethanol | | 34 | 34 | 34 | 34 | 34 | 35 | 29 | 29 | 29 |
| Isopropanol | | | | | 10 | | | | | |
| PG | | | | | | 10 | 5 | 10 | 5 | 5 |
| Transcutol | | | | | | | 5 | 5 | 10 | 5 |
| Water | | 49 | 39.5 | 40 | 39 | 39 | 38 | 39 | 39 | 46.5 |
| Lactic Acid | | 1.5 | 1 | 1.5 | 1.5 | 1.5 | 1.5 | 1.5 | 1.5 | 1.5 |

TABLE 9

| Ingredients: | IB949 (Percentages in (w/w)) |
|---|---|
| Ibuprofen | 5.0 |
| Ethanol | 30 |
| Propylene glycol | 10.0 |
| Triethyl citrate | 2.0 |
| Diethylene glycol monoethyl ether [or (2-(2-ethoxyethoxy)ethanol); Transcutol] | 14.0 |
| Sodium lauryl sulfate | 2.0 |
| D,L-Lactic acid | 1.5 |
| Propyl paraben | 0.1 |
| Methyl paraben | 0.1 |
| Hydroxypropyl cellulose, HY 121 | 2.0 |
| Water | 33.3 |

TABLE 10

| Ingredients | F1 (Ibugel ™) | F2 (IB949) | F3 | F4 | F5 | F6 | F7 | F8 | F9 |
|---|---|---|---|---|---|---|---|---|---|
| Transcutol | | 14 | 14 | 14 | 14 | 14 | 14 | 14 | 14 |
| Propylene glycol | | 10 | 10 | 10 | 10 | 10 | 10 | 10 | 10 |
| Triethyl citrate | | 2 | 2 | 2 | 2 | 2 | 2 | 1 | 0.5 |
| Sodium Lauryl sulfate | | 2 | 3 | 1 | 2 | 2 | 2 | 2 | 2 |
| Ethanol | | 30 | 30 | 30 | 30 | 30 | 30 | 30 | 30 |
| Water | | 33.3 | 32.3 | 34.3 | 34.3 | 33.8 | 32.8 | 34.3 | 34.8 |
| D,L-Lactic acid | | 1.5 | 1.5 | 1.5 | 0.5 | 1 | 2 | 1.5 | 1.5 |
| Propyl paraben | | 0.1 | 0.1 | 0.1 | 0.1 | 0.1 | 0.1 | 0.1 | 0.1 |
| Methyl paraben | | 0.1 | 0.1 | 0.1 | 0.1 | 0.1 | 0.1 | 0.1 | 0.1 |
| Ibuprofen | | 5 | 5 | 5 | 5 | 5 | 5 | 5 | 5 |
| Hydroxypropyl cellulose, HY 121 | | 2 | 2 | 2 | 2 | 2 | 2 | 2 | 2 |

TABLE 11

| Formulation | F1 Ibugel | F2 | F3 | F4 | F5 | F6 | F7 | F8 | F9 |
|---|---|---|---|---|---|---|---|---|---|
| 4 hrs | 0.3 | 2.6 | 0.7 | 1.1 | 1.4 | 1.1 | 1.3 | 0.6 | 1.4 |
| SE | 0.1 | 0.8 | 0.1 | 0.3 | 0.7 | 0.4 | 0.8 | 0.3 | 0.3 |
| 21 hrs | 11.8 | 36.8 | 24.7 | 28.7 | 25.8 | 33.2 | 29.3 | 23.8 | 29.8 |
| SE | 2 | 6.9 | 4.6 | 4.9 | 4.9 | 5.4 | 5.7 | 2.6 | 2.6 |

Accumulated dose in (μg/cm2)

TABLE 11-continued

| | Accumulated dose in (μg/cm2) | | | | | | | | |
|---|---|---|---|---|---|---|---|---|---|
| Formulation | F1 Ibugel | F2 | F3 | F4 | F5 | F6 | F7 | F8 | F9 |
| 24 hrs | 14.4 | 39.4 | 27.2 | 31.2 | 28.3 | 35.8 | 32.7 | 26.2 | 32.6 |
| SE | 1.9 | 7.3 | 4.7 | 5.2 | 5.1 | 5.6 | 5.2 | 2.9 | 2.8 |
| 24 hrs ER | 1 | 2.7 | 1.9 | 2.2 | 2 | 2.5 | 2.3 | 1.8 | 2.3 |
| SE | 0.3 | 0.9 | 0.6 | 0.7 | 0.6 | 0.7 | 0.7 | 0.4 | 0.5 |

SE = standard error;
ER = Enhancement Ratio

TABLE 12

| rpm | F2 | F3 | F4 | F5 | F6 | F7 | F8 | F9 |
|---|---|---|---|---|---|---|---|---|
| 0.5 | 19,196 | 25,375 | 23,695 | 25,675 | 22,015 | 34,773 | 26,094 | 27,054 |
| 0.6 | 18,396 | 24,345 | 22,295 | 23,445 | 21,245 | 26,664 | 24,845 | 25,295 |
| 0.7 | 17,782 | 23,438 | 21,595 | 22,881 | 20,053 | 25,923 | 23,352 | 23,995 |
| 0.8 | 17,284 | 22,570 | 20,808 | 22,420 | 19,383 | 24,820 | 22,308 | 22,983 |
| 0.9 | 16,463 | 21,829 | 20,196 | 21,662 | 18,929 | 21,529 | 21,529 | 21,995 |

TABLE 13

| | Formulation name | | | | | |
|---|---|---|---|---|---|---|
| Ingredients | Ibugel wt/wt % | Ib949 wt/wt % | Ibct1pH wt/wt % | Ibct1 wt/wt % | Ibct9pH wt/wt % | Ibct9 wt/wt % |
| Ibuprofen | 5 | 5 | 5 | 5 | 5 | 5 |
| Transcutol | | 14 | 14 | 14 | 14 | 14 |
| PG | | 10 | 10 | 10 | 10 | 10 |
| Triethyl Citrate | | 2 | 2 | 2 | 2 | 2 |
| Na Lauryl Sulphate | | 2 | 2 | 2 | 2 | 2 |
| Ethanol | | 30 | 30 | 30 | 30 | 30 |
| Water | | 33.3 | | | | |
| 50 mM citrate pH 4.2 | | | 33.3 | 33.3 | | |
| 50 mM citrate pH 4.8 | | | | | 33.3 | 33.3 |
| PP | | 0.1 | 0.1 | 0.1 | 0.1 | 0.1 |
| MP | | 0.1 | 0.1 | 0.1 | 0.1 | 0.1 |
| Lactic Acid | | 1.5 | 1.5 | 1.5 | 1.5 | 1.5 |
| HY 121 | | 2 | 2 | 2 | 2 | 2 |
| pH | | 4.27 | 4.18 | 4.29 | 4.29 | 4.9 |

TABLE 14

| | Formulation name | | | | | | | | |
|---|---|---|---|---|---|---|---|---|---|
| Ingredients | Ibugel wt/wt % | IbCt1 wt/wt % | IbCt1pH wt/wt % | IbCt4 wt/wt % | IbCt4pH wt/wt % | IbCt17 wt/wt % | IbCt17pH wt/wt % | IbCt20 wt/wt % | IbCt20pH wt/wt % |
| Ibuprofen | 5 | 5 | 5 | 5 | 5 | 5 | 5 | 5 | 5 |
| Transcutol | | 14 | 14 | 14 | 14 | 14 | 14 | 14 | 14 |
| PG | | 10 | 10 | 10 | 10 | 10 | 10 | 10 | 10 |
| Triethyl Citrate | | 2 | 2 | 2 | 2 | 2 | 2 | 2 | 2 |
| Na Lauryl Sulphate | | 2 | 2 | 2 | 2 | 2 | 2 | 2 | 2 |
| Ethanol | | 30 | 30 | 30 | 30 | 30 | 30 | 30 | 30 |
| 50 mM citrate pH 4.2 | | 33.3 | 33.3 | 34.3 | 34.3 | | | | |
| 100 mM citrate pH 4.2 | | | | | | 33.3 | 33.3 | 34.3 | 34.3 |
| PP | | 0.1 | 0.1 | 0.1 | 0.1 | 0.1 | 0.1 | 0.1 | 0.1 |
| MP | | 0.1 | 0.1 | 0.1 | 0.1 | 0.1 | 0.1 | 0.1 | 0.1 |
| Lactic Acid | | 1.5 | 1.5 | 0.5 | 0.5 | 1.5 | 1.5 | 0.5 | 0.5 |
| HY 121 | | 2 | 2 | 2 | 2 | 2 | 2 | 2 | 2 |

TABLE 15

| Ingredients | Ibugel wt/wt % | Ib949 wt/wt % | Ib950 wt/wt % | Ib951 wt/wt % | Ib952 wt/wt % | Ib953 wt/wt % | Ib954 wt/wt % | Ib955 wt/wt % | Ib956 wt/wt % |
|---|---|---|---|---|---|---|---|---|---|
| Ibuprofen | 5 | 5 | 5 | 5 | 5 | 5 | 5 | 5 | 5 |
| Transcutol | | 14 | 14 | 14 | 14 | 14 | 14 | 14 | 14 |
| PG | | 10 | 10 | 10 | 10 | 10 | 10 | 10 | 10 |
| Triethyl Citrate | | 2 | 2 | 2 | 2 | 2 | 2 | 1 | 0.5 |
| Na Lauryl Sulphate | | 2 | 3 | 1 | 2 | 2 | 2 | 2 | 2 |
| Ethanol | | 30 | 30 | 30 | 30 | 30 | 30 | 30 | 30 |
| Water | | 33.3 | 32.3 | 34.3 | 34.3 | 33.8 | 32.8 | 34.3 | 34.8 |
| PP | | 0.1 | 0.1 | 0.1 | 0.1 | 0.1 | 0.1 | 0.1 | 0.1 |
| MP | | 0.1 | 0.1 | 0.1 | 0.1 | 0.1 | 0.1 | 0.1 | 0.1 |
| Lactic Acid | | 1.5 | 1.5 | 1.5 | 0.5 | 1 | 2 | 1.5 | 1.5 |
| HY 121 | | 2 | 2 | 2 | 2 | 2 | 2 | 2 | 2 |
| pH | 4.35 | 4.02 | 3.88 | 4.24 | 4.03 | 3.89 | 4.6 | 4.7 | |

TABLE 16

| Ingredients | Ibugel wt/wt % | Ib949 wt/wt % | IbCt1pH wt/wt % | IbCt2pH wt/wt % | IbCt3pH wt/wt % | IbCt4pH wt/wt % | IbCt5pH wt/wt % | IbCt6pH wt/wt % | IbCt7pH wt/wt % | IbCt8pH wt/wt % |
|---|---|---|---|---|---|---|---|---|---|---|
| Ibuprofen | 5 | 5 | 5 | 5 | 5 | 5 | 5 | 5 | 5 | 5 |
| Transcutol | | 14 | 14 | 14 | 14 | 14 | 14 | 14 | 14 | 14 |
| PG | | 10 | 10 | 10 | 10 | 10 | 10 | 10 | 10 | 10 |
| Triethyl Citrate | | 2 | 2 | 2 | 2 | 2 | 2 | 2 | 1 | 0.5 |
| Na Lauryl Sulphate | | 2 | 2 | 3 | 1 | 2 | 2 | 2 | 2 | 2 |
| Ethanol | | 30 | 30 | 30 | 30 | 30 | 30 | 30 | 30 | 30 |
| Water | | 33.3 | | | | | | | | |
| 50 mM citrate pH 4.2 | | | 33.3 | 32.3 | 34.3 | 34.3 | 33.8 | 32.8 | 34.3 | 34.8 |
| PP | | 0.1 | 0.1 | 0.1 | 0.1 | 0.1 | 0.1 | 0.1 | 0.1 | 0.1 |
| MP | | 0.1 | 0.1 | 0.1 | 0.1 | 0.1 | 0.1 | 0.1 | 0.1 | 0.1 |
| Lactic Acid | | 1.5 | 1.5 | 1.5 | 1.5 | 0.5 | 1 | 2 | 1.5 | 1.5 |
| HY 121 | | 2 | 2 | 2 | 2 | 2 | 2 | 2 | 2 | 2 |
| pH | 4.3 | 4.39 | 4.25 | 4.3 | 4.31 | 4.28 | 4.33 | 4.32 | 4.15 | |

TABLE 17

| Ingredients | Ibugel wt/wt % | Ib949 wt/wt % | Ibct1pH wt/wt % | Ibct1 wt/wt % | Ibct9pH wt/wt % | Ibct9 wt/wt % |
|---|---|---|---|---|---|---|
| Ibuprofen | 5 | 5 | 5 | 5 | 5 | 5 |
| Transcutol | | 14 | 14 | 14 | 14 | 14 |
| PG | | 10 | 10 | 10 | 10 | 10 |
| Triethyl Citrate | | 2 | 2 | 2 | 2 | 2 |
| Na Lauryl Sulphate | | 2 | 2 | 2 | 2 | 2 |
| Ethanol | | 30 | 30 | 30 | 30 | 30 |
| Water | | 33.3 | | | | |
| 50 mM citrate pH 4.2 | | | 33.3 | 33.3 | | |
| 50 mM citrate pH 4.8 | | | | | 33.3 | 33.3 |
| PP | | 0.1 | 0.1 | 0.1 | 0.1 | 0.1 |
| MP | | 0.1 | 0.1 | 0.1 | 0.1 | 0.1 |
| Lactic Acid | | 1.5 | 1.5 | 1.5 | 1.5 | 1.5 |
| HY 121 | | 2 | 2 | 2 | 2 | 2 |
| pH | | 4.27 | 4.18 | 4.29 | 4.29 | 4.9 |

TABLE 18

| Ingredients | Formulation | | | | | | | | | | |
|---|---|---|---|---|---|---|---|---|---|---|---|
| | Ib949 | Ib949-1 | Ib949-2 | Ib949-3 | Ib949-4 | Ib949-5 | Ib949-6 | Ib949-7 | Ib949-8 | Ib949-2* | Ib949-9 |
| Transcutol | 14 | 14 | 14 | 14 | 14 | 14 | 14 | 14 | 14 | 14 | 14 |
| Propylene glycol | 10 | 10 | 10 | 10 | 10 | 10 | 10 | 10 | 10 | 10 | 10 |
| Triethyl citrate | 2 | 2 | 2 | 0 | 0 | 0 | 0 | 0 | 2 | 2 | 2 |
| Na Lauryl sulfate | 2 | 2 | 0 | 2 | 2 | 0 | 0 | 0 | 2 | 0 | 0 |
| Ethanol | 30 | 30 | 30 | 30 | 30 | 30 | 30 | 30 | 30 | 30 | 30 |
| Water | qs 100 | qs 100 | qs 100 | qs 100 | qs 100 | qs 100 | qs 100 | qs 100 | qs 100 | qs 100 | qs 100 |
| Lactic acid | 1.5 | 0 | 0 | 1.5 | 0 | 0 | 0 | 0 | 1.5 | 0 | 0 |
| Propyl paraben | 0.1 | 0.1 | 0.1 | 0.1 | 0.1 | 0.1 | 0 | 0 | 0.1 | 0.1 | 0 |
| Methyl paraben | 0.1 | 0.1 | 0.1 | 0.1 | 0.1 | 0.1 | 0 | 0 | 0.1 | 0.1 | 0 |
| Ibuprofen | 5 | 5 | 5 | 5 | 5 | 5 | 5 | 0 | 1 | 5 | 0 |
| HPC HY121 | 2 | 2 | 2 | 2 | 2 | 2 | 2 | 2 | 2 | 2 | 2 |
| pH | 4.45 | 3.95 | 3.65 | 3.38 | 4.17 | 3.4 | 3.48 | 4.99 | 3.33 | 3.41 | 4.18 |

*pH of Ib949-2 was measured 2 days later

TABLE 19

| Viscosity with spindle 31 RPM speed | Ib949-1 (cP) | Ib949-2 (cP) | Ib949-3 (cP) | Ib949-4 (cP) | Ib949-5 (cP) | Ib949-6 (cP) | Ib949-7 (cP) | Ib949-8 (cP) | Ib949-9 (cP) | Ib949-9 (cP) |
|---|---|---|---|---|---|---|---|---|---|---|
| 0.5 | 19016 | 15837 | 18116 | 18656 | 11817 | 21235 | 13737 | 22135 | 13497 | 13497 |
| 0.6 | 18346 | 15047 | 16696 | 17446 | 10848 | 20096 | 13547 | 20496 | 12547 | 12547 |
| 0.7 | 17953 | 14440 | 16111 | 17182 | 10755 | 19025 | 13326 | 19453 | 12340 | 12340 |
| 0.8 | 17471 | 13947 | 15672 | 16759 | 10485 | 18071 | 12860 | 18709 | 11698 | 11698 |
| 0.9 | 16963 | 13297 | 15230 | 16430 | 10130 | 17330 | 12431 | 17863 | 11464 | 11464 |

TABLE 20

| Ingredients | Ib949 | Transcutol | PG | Triethyl Citrate | Na Lauryl Sulfate | Ethanol | Lactic Acid | PP | MP | HY121 |
|---|---|---|---|---|---|---|---|---|---|---|
| Transcutol | 14 | 14 | | | | | | | | |
| PG | 10 | | 10 | | | | | | | |
| Triethyl citrate | 2 | | | 2 | | | | | | |
| Na Lauryl sulfate | 2 | | | | 2 | | | | | |
| Ethanol | 30 | | | | | 30 | | | | |
| Water | | 86 | 90 | 98 | 98 | 70 | 98.5 | 99.9 | 99.9 | 98 |
| Lactic acid | 1.5 | | | | | | 1.5 | | | |
| PP | 0.1 | | | | | | | 0.1 | | |
| MP | 0.1 | | | | | | | | 0.1 | |
| HY121 | 2 | | | | | | | | | 2 |
| pH- water | | 7.72 | 7.73 | 7.86 | 7.75 | 7.89 | 7.75 | 7.67 | 7.65 | 7.58 |
| pH-water and ingredients | | 4.32 | 6.97 | 3.72 | 7.97 | 7.31 | 2.4 | 6.13 | 5.72 | 6.43 |

TABLE 21

| Ingredients | Formulation name | | | | | | | | |
|---|---|---|---|---|---|---|---|---|---|
| | Ibugel wt/wt % | Ib949 wt/wt % | Ib950 wt/wt % | Ib951 wt/wt % | Ib952 wt/wt % | Ib953 wt/wt % | Ib954 wt/wt % | Ib955 wt/wt % | Ib956 wt/wt % |
| Ibuprofen | 5 | 5 | 5 | 5 | 5 | 5 | 5 | 5 | 5 |
| Transcutol | | 14 | 14 | 14 | 14 | 14 | 14 | 14 | 14 |
| PG | | 10 | 10 | 10 | 10 | 10 | 10 | 10 | 10 |
| Triethyl Citrate | | 2 | 2 | 2 | 2 | 2 | 2 | 1 | 0.5 |

TABLE 21-continued

| Ingredients | Ibugel wt/wt % | Ib949 wt/wt % | Ib950 wt/wt % | Ib951 wt/wt % | Ib952 wt/wt % | Ib953 wt/wt % | Ib954 wt/wt % | Ib955 wt/wt % | Ib956 wt/wt % |
|---|---|---|---|---|---|---|---|---|---|
| Na Lauryl Sulphate | | 2 | 3 | 1 | 2 | 2 | 2 | 2 | 2 |
| Ethanol | | 30 | 30 | 30 | 30 | 30 | 30 | 30 | 30 |
| Water | | 33.3 | 32.3 | 34.3 | 34.3 | 33.8 | 32.8 | 34.3 | 34.8 |
| PP | | 0.1 | 0.1 | 0.1 | 0.1 | 0.1 | 0.1 | 0.1 | 0.1 |
| MP | | 0.1 | 0.1 | 0.1 | 0.1 | 0.1 | 0.1 | 0.1 | 0.1 |
| Lactic Acid | | 1.5 | 1.5 | 1.5 | 0.5 | 1 | 2 | 1.5 | 1.5 |
| HY 121 | | 2 | 2 | 2 | 2 | 2 | 2 | 2 | 2 |

TABLE 22

| | RPM | Visc spindle #63 | RPM | Visc spindle #64 |
|---|---|---|---|---|
| Ib949 | 10 | 1344 | 10 | 6239 |
| | 15 | 1160 | 15 | 5439 |
| | 20 | 1074 | 20 | 4979 |
| | 25 | 989 | 25 | 4583 |
| | 30 | 916 | 30 | 4279 |
| Ib950 | 10 | 1356 | 10 | 7318 |
| | 15 | 1184 | 15 | 6279 |
| | 20 | 1080 | 20 | 5729 |
| | 25 | 993 | 25 | 5327 |
| | 30 | 924 | 30 | 4819 |
| Ib951 | 10 | 1248 | 10 | 6659 |
| | 15 | 1088 | 15 | 5759 |
| | 20 | 1008 | 20 | 5279 |
| | 25 | 931 | 25 | 4823 |
| | 30 | 860 | 30 | 4479 |
| Ib952 | 10 | 1368 | 10 | 7318 |
| | 15 | 1192 | 15 | 6359 |
| | 20 | 1092 | 20 | 5789 |
| | 25 | 1013 | 25 | 5351 |
| | 30 | 944 | 30 | 4979 |
| Ib953 | 10 | 1380 | 10 | 7318 |
| | 15 | 1200 | 15 | 6359 |
| | 20 | 1098 | 20 | 5789 |
| | 25 | 1017 | 25 | 5351 |
| | 30 | 944 | 30 | 4979 |
| Ib954 | 10 | 5291 | 10 | 24955 |
| | 15 | 4359 | 15 | 21555 |
| | 20 | 3755 | 20 | 19016 |
| | 25 | 3345 | 25 | 16892 |
| | 30 | 3027 | 30 | 15517 |
| Ib955 | 20 | 1380 | 20 | 7138 |
| | 25 | 1200 | 25 | 6199 |
| | 30 | 1098 | 30 | 5699 |
| | 35 | 1022 | 35 | 5303 |
| | 40 | 944 | 40 | 4979 |
| Ib956 | 20 | 1406 | 20 | 7258 |
| | 25 | 1224 | 25 | 6319 |
| | 30 | 1120 | 30 | 5759 |
| | 35 | 1032 | 35 | 5327 |
| | 40 | 956 | 40 | 4959 |

| Formulation | Ib949 | Ib950 | Ib951 | Ib952 |
|---|---|---|---|---|
| pH | 4.05 | 4.02 | 3.88 | 4.24 |

| Formulation | Ib953 | Ib954 | Ib955 | Ib956 |
|---|---|---|---|---|
| pH | 4.03 | 3.89 | 4.6 | 4.7 |

TABLE 23

| Ingredients | wt/wt % |
|---|---|
| Ibuprofen | 5 |
| PBS* | 30.3 |
| EtOH | 30 |
| PG | 4 |
| Amphosol | 5 |
| Transcutol | 20 |
| Lactic Acid | 1.5 |
| Triethyl Citrate | 2 |
| Methyl Paraben | 0.1 |
| Propyl Paraben | 0.1 |
| HPC HY121 | 2 |

*The gel formulation is prepared in a PBS buffered system with the final pH adjusted to ~6.5

The invention claimed is:

1. A composition comprising ibuprofen, a hydroalcoholic-based solvent, a $C_{1-4}$ alcohol ester of citric acid, and a surfactant, wherein the composition is formulated for topical administration.

2. The composition of claim 1, comprising about 0.1% (w/w) to about 10% (w/w), about 0.5% (w/w) to about 9.0% (w/w), about 1.0% (w/w) to about 8.0% (w/w), about 2.0% (w/w) to about 7.0% (w/w), about 3.0% (w/w) to about 6.5% (w/w), about 4.0% (w/w) to about 6.0% (w/w), or about 5% (w/w) of ibuprofen.

3. The composition of claim 1, wherein the $C_{1-4}$ alcohol ester of citric acid is a compound of the formula:

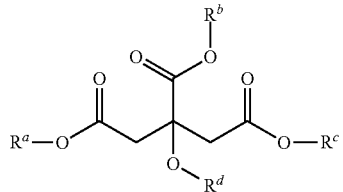

wherein $R^a$, $R^b$ and $R^c$ are the same and are selected from methyl, ethyl, propyl, butyl, isopropyl, isobutyl and t-butyl and $R^d$ is selected from the group consisting of H and methyl.

4. The composition of claim 1, wherein the $C_{1-4}$ alcohol ester of citric acid is triethyl citrate.

5. The composition of claim 1, comprising about 0.5% (w/w) to about 5% (w/w), about 1.5% (w/w) to about 4.5% (w/w), about 2.0% (w/w) to about 4.0% (w/w) or about 3% (w/w), of the $C_{1-4}$ alcohol ester of citric acid.

6. The composition of claim 1, wherein the surfactant is an anionic surfactant or a zwitterionic surfactant, or a mixture thereof, and wherein the anionic surfactant is selected from the group consisting of sodium lauryl sulfate, ammonium lauryl sulfate, sodium dodecyl sulfate, and mixtures thereof.

7. The composition of claim 1, comprising about 0.5% (w/w) to about 20% (w/w), about 0.75% (w/w) to about 15% (w/w), 1.0% (w/w) to about 10% (w/w), about 1.5% (w/w) to about 9% (w/w), or about 2.0% (w/w) to about 8.0% (w/w) of one or more surfactants.

8. The composition of claim 6, wherein the zwitterionic surfactant is an N-(cocoalkyl)amidopropyl betaine.

9. The composition of claim 1, comprising about 10% (w/w) to about 60% (w/w), about 15% (w/w) to about 55% (w/w), or about 20% (w/w) to about 50% (w/w) of water, and about 10% (w/w) to about 60% (w/w), about 15% (w/w) to about 55% (w/w), or about 20% (w/w) to about 50% (w/w) of alcohol.

10. The composition of claim 9, wherein the alcohol is selected from the group consisting of ethanol, isopropanol, 2-(2-ethoxyethoxy)ethanol(transcutol), and mixtures thereof.

11. The composition of claim 10, additionally comprising a diol.

12. The composition of claim 11, wherein the diol is selected from the group consisting of propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, and mixtures thereof.

13. The composition of claim 12, wherein the diol is propylene glycol.

14. The composition of claim 12, comprising about 0% (w/w) to about 20% (w/w), about 1.0% (w/w) to about 15% (w/w), or about 4% (w/w) to about 15% (w/w) of propylene glycol.

15. The composition of claim 1, comprising at least one thickening agent selected from the group consisting of hydroxypropyl cellulose (HPC), hydroxypropyl methyl cellulose, hydroxyethyl cellulose, hydroxyethyl methyl cellulose, ethyl cellulose, methyl cellulose, carboxymethyl cellulose, dextran, guar gum, pectin, starch, cellulose, and mixtures thereof.

16. The composition of claim 1, comprising ibuprofen, ethanol, water, triethyl citrate, lactic acid, transcutol, propylene glycol and N-(cocoalkyl)amidopropyl betaine.

17. The composition of claim 16, comprising:
about 1% (w/w) to about 10% (w/w) ibuprofen;
about 25% (w/w) to about 35% (w/w) ethanol;
about 15% (w/w) to about 25% (w/w) transcutol;
about 1% (w/w) to about 10% (w/w) propylene glycol;
about 25% (w/w) to about 35% (w/w) water;
about 2% (w/w) to about 5% (w/w) triethyl citrate;
about 0.5% (w/w) to about 2.5% (w/w) lactic acid; and
about 2% (w/w) to about 10% (w/w) N-(cocoalkyl)amidopropyl betaine.

18. The composition of claim 16, wherein the water component is buffered.

19. The composition of claim 18, additionally comprising a cellulosic thickening agent in an amount of about 0.5% (w/w) to about 2.0% (w/w).

20. A method for treating pain comprising applying an effective amount of a composition comprising ibuprofen, a hydroalcoholic-based solvent, a $C_{1-4}$ alcohol ester of citric acid and a surfactant, wherein the composition is formulated for topical administration, to a subject in need thereof.

* * * * *

UNITED STATES PATENT AND TRADEMARK OFFICE
CERTIFICATE OF CORRECTION

PATENT NO. : 8,470,886 B2  
APPLICATION NO. : 13/511287  
DATED : June 25, 2013  
INVENTOR(S) : Dominic King-Smith et al.

Page 1 of 1

It is certified that error appears in the above-identified patent and that said Letters Patent is hereby corrected as shown below:

In the Specifications

Column 1, line 22, please replace "dysmenorrheal" with --dysmenorrhea--.

Column 2, line 51, please replace "flux than a currently" with --flux than currently--.

Column 17, line 38, please replace "6.5" with --6.5.--.

Column 21, line 10, please replace "C." with --C--.

Column 21, line 46, please replace "Ibugel™" with --Ibugel™.--.

Column 23, line 25, please replace "laurel" with --lauryl--.

Column 24, line 24, replace "diisoproply" with --diisopropyl--.

In the Claims

Column 40, claim 4, line 57, please replace "$C_{IA}$" with --$C_{1-4}$--.

Column 41, claim 14, line 28, please replace "The composition of claim 12," with --The composition of claim 13,--.

Signed and Sealed this  
Sixth Day of May, 2014

Michelle K. Lee  
*Deputy Director of the United States Patent and Trademark Office*